US012799056B2

(12) United States Patent
Hallinan et al.

(10) Patent No.: US 12,799,056 B2
(45) Date of Patent: Nov. 17, 2026

(54) CONTROL OF IODIDES IN ACETIC ACID PRODUCTION

(71) Applicant: LyondellBasell Acetyls, LLC, Houston, TX (US)

(72) Inventors: Noel C. Hallinan, Loveland, OH (US); David L. Ramage, Friendswood, TX (US); Daniel F. White, Houston, TX (US)

(73) Assignee: LyondellBasell Acetyls, LLC, Houston, TX (US)

(*) Notice: Subject to any disclaimer, the term of this patent is extended or adjusted under 35 U.S.C. 154(b) by 476 days.

(21) Appl. No.: 18/436,505

(22) Filed: Feb. 8, 2024

(65) Prior Publication Data

US 2024/0279144 A1 Aug. 22, 2024

Related U.S. Application Data

(60) Provisional application No. 63/444,770, filed on Feb. 10, 2023.

(51) Int. Cl.
*C07C 29/44* (2006.01)
*C07C 29/94* (2006.01)

(52) U.S. Cl.
CPC .............. *C07C 29/44* (2013.01); *C07C 29/94* (2013.01)

(58) Field of Classification Search
CPC ......... C07C 29/44; C07C 29/94; C07C 51/12; C07C 51/50; C07C 53/08; B01J 23/38; B01J 27/14
See application file for complete search history.

(56) References Cited

U.S. PATENT DOCUMENTS

| | | | | |
|---|---|---|---|---|
| 3,818,060 | A | 6/1974 | Forster et al. | |
| 4,640,802 | A * | 2/1987 | Drent | C07C 51/12 560/111 |
| 4,670,570 | A * | 6/1987 | Wegman | C07C 51/12 556/18 |
| 5,416,237 | A | 5/1995 | Aubigne et al. | |
| 5,817,869 | A | 10/1998 | Hinnenkamp et al. | |
| 5,932,764 | A | 8/1999 | Morris et al. | |
| 6,031,129 | A | 2/2000 | Hinnenkamp et al. | |
| 6,472,558 | B1 | 10/2002 | Key et al. | |

(Continued)

FOREIGN PATENT DOCUMENTS

| | | | | |
|---|---|---|---|---|
| EP | 0171652 A1 | 2/1986 | | |
| EP | 0114703 * | 10/1986 | | C07C 51/12 |

(Continued)

OTHER PUBLICATIONS

International Search Report dated Jul. 15, 2024 of International Application No. PCT/US2024/014973.

*Primary Examiner* — Yate' K Cutliff

(57) ABSTRACT

A process for producing and recovering acetic acid in an acetic acid production system is disclosed, the process comprising contacting methanol and carbon monoxide in the presence of a liquid reaction medium comprising iodide under carbonylation conditions sufficient to form acetic acid. The liquid reaction medium comprises a carbonylation catalyst, water, and an additive comprising a bidentate phosphine dioxide, a tertiary arsine oxide, or a combination thereof. An aspect of the process includes a method for reducing water in an acetic acid production process.

20 Claims, 5 Drawing Sheets

(56) References Cited

U.S. PATENT DOCUMENTS

| | | | | |
|---|---|---|---|---|
| 6,552,221 | B1 | 4/2003 | Hallinan et al. | |
| 7,524,988 | B2 | 4/2009 | Harris et al. | |
| 8,076,512 | B2 | 12/2011 | Fitzpatrick et al. | |
| 9,102,612 | B2 * | 8/2015 | Hallinan | C07C 51/50 |
| 9,475,746 | B2 | 10/2016 | Hallinan et al. | |
| 9,790,159 | B2 | 10/2017 | Hallinan et al. | |
| 10,067,113 | B2 * | 9/2018 | Hallinan | G01N 33/20 |

FOREIGN PATENT DOCUMENTS

| | | | |
|---|---|---|---|
| EP | 0114703 | B1 | 10/1986 |
| EP | 0133331 | B1 | 11/1986 |
| GB | 1406672 | A | 9/1975 |
| JP | 5544127 | B2 | 7/2014 |

* cited by examiner

CONTROL OF IODIDES IN ACETIC ACID PRODUCTION

CROSS-REFERENCE TO RELATED APPLICATIONS

The application claims the benefit of priority to U.S. Provisional Patent Application No. 63/444,770 filed on Feb. 10, 2023, which is incorporated herein by reference in its entirety.

FIELD OF THE INVENTION

This disclosure relates to the production of acetic acid. More particularly, the disclosure relates to management of hydrogen iodide (HI) levels in acetic acid production.

BACKGROUND OF THE INVENTION

In the current acetic acid production process, a reaction mixture is withdrawn from a reactor and is separated in a flash tank into a liquid fraction and a vapor fraction comprising acetic acid generated during the carbonylation reaction. The liquid fraction may be recycled to the carbonylation reactor, and the vapor fraction is passed to a separations unit, which by way of example may be a light-ends distillation column. The light-ends distillation column separates a crude acetic acid product from other components. The crude acetic acid product is passed to a drying column to remove water and then is subjected to further separations to recover acetic acid.

Hydrogen iodide (HI) can be a reaction component in the production of acetic acid. Although process equipment generally used in the production of acetic acid is substantially inert to the reaction components, the equipment can still be corroded or otherwise adversely affected by HI. Additionally, HI can lead to the formation of long-chain alkyl iodide impurities, e.g., hexyl iodide, which are difficult to remove and which may complicate the recovery of acetic acid. Thus, the presence of HI can have consequences both in terms of corrosion of processing equipment and in terms of contamination of a final acetic acid product.

Processes for managing HI exist; however, there continues to be a need to improve upon, and provide alternatives to, current processes for managing levels of HI.

SUMMARY OF THE INVENTION

In some embodiments, a process for producing acetic acid in an acetic acid production system, comprises contacting methanol and carbon monoxide in the presence of a liquid reaction medium comprising iodide under carbonylation conditions sufficient to form acetic acid. The liquid reaction medium comprises a carbonylation catalyst, water, and an additive. The carbonylation catalyst is selected from the group consisting of rhodium catalysts, iridium catalysts and palladium catalysts. The water is present in the liquid reaction medium in the range of from 0.1 wt % to 10 wt %, based on the weight of the liquid reaction medium. The additive is present in the liquid reaction medium at an additive to iodide molar ratio of 0.01:1 to 5.0:1, along with in-situ generated derivatives of the additive, and/or combinations thereof. The additive comprises a bidentate phosphine dioxide, a tertiary arsine oxide, or a combination thereof. The process further comprises recovering the acetic acid.

In some embodiments, a method for reducing water in an acetic acid production process comprises contacting methanol and carbon monoxide in the presence of a liquid reaction medium comprising a first amount of hydrogen iodide, under carbonylation conditions sufficient to form acetic acid. The liquid reaction medium comprises a carbonylation catalyst, selected from the group consisting of rhodium catalysts, iridium catalysts and palladium catalysts and a first amount of water, sufficient to form an azeotropic mixture of the first amount of hydrogen iodide and the first amount of water. The method further comprises adding an additive to the liquid reaction medium at an additive to iodide molar ratio of 0.01:1 to 5.0:1, wherein the additive forms a complex with at least a portion of the first amount of hydrogen iodide resulting in a second amount of hydrogen iodide. The additive comprises a bidentate phosphine dioxide, a tertiary arsine oxide, or a combination thereof. The method further comprises reducing the water in the liquid reaction medium to a second amount of water while maintaining an azeotropic mixture of the second amount of hydrogen iodide and the second amount of water.

The above paragraphs present a simplified summary of the presently disclosed subject matter in order to provide a basic understanding of some aspects thereof. The summary is not an exhaustive overview, nor is it intended to identify key or critical elements to delineate the scope of the subject matter claimed below. Its sole purpose is to present some concepts in a simplified form as a prelude to the more detailed description set forth below.

BRIEF DESCRIPTION OF THE DRAWINGS

The claimed subject matter may be understood by reference to the following description taken in conjunction with the accompanying drawings, in which like reference numerals identify like elements, and in which:

Figure 1:
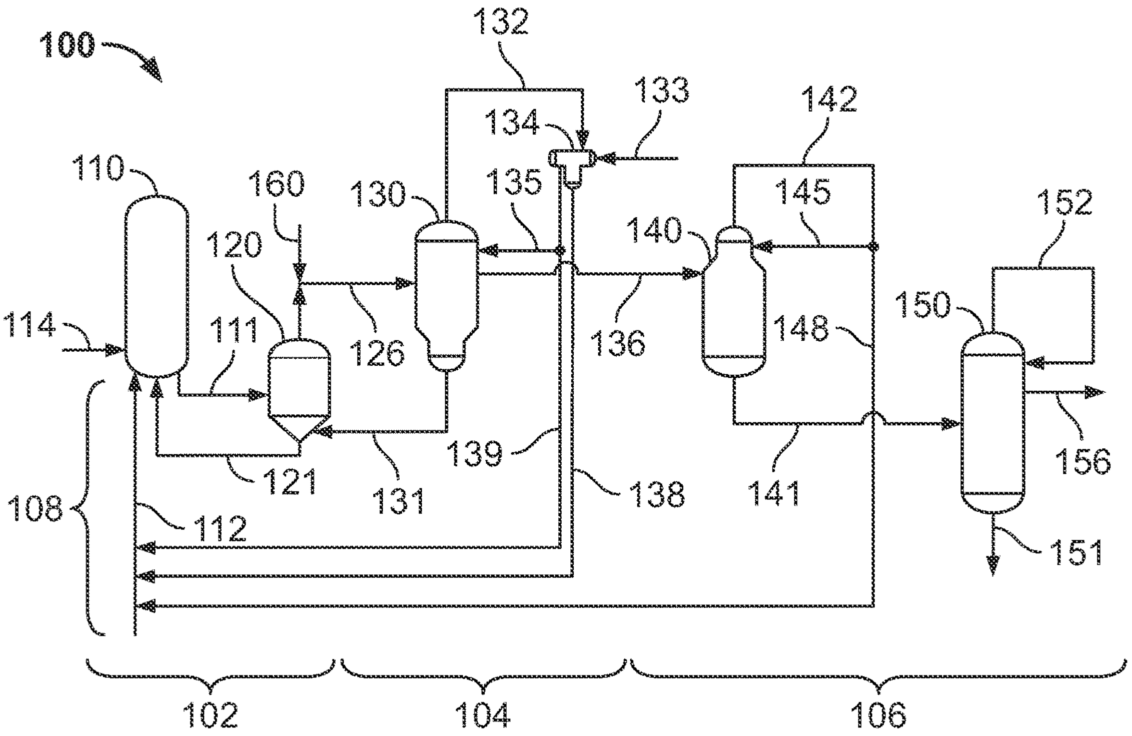
FIG. 1 is a schematic of an exemplary acetic acid production system in accordance with embodiments and/or techniques disclosed herein.

While the disclosed process and system are susceptible to various modifications and alternative forms, the drawings illustrate specific embodiments herein described in detail by way of example. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE INVENTION

A detailed description of embodiments of the disclosed process follows. However, it is to be understood that the described embodiments are merely exemplary of the process and that the process may be embodied in various and alternative forms of the described embodiments. Therefore, specific procedural, structural and functional details which are addressed in the embodiments described herein are not to be interpreted as limiting, but merely as a basis for the claims and as a representative basis for teaching one skilled in the art to variously employ the disclosed process.

The designation of groups of the Periodic Table of the Elements as used herein is in accordance with the current IUPAC convention. The expression "HAc" is used herein as an abbreviation for acetaldehyde. The expression "Mel" is used herein as an abbreviation for methyl iodide. The expression "HI" is used herein as an abbreviation for hydrogen iodide. The expression "acac" is used herein as an abbreviation for acetoacetate anion, i.e., $H_3CC(=O)CH_2C(=O)O—$. Unless specifically indicated otherwise, the expression "wt %" as used herein refers to the percentage by weight of a particular component in the referenced composition. With respect to all ranges disclosed herein, such ranges are intended to include any combination of the mentioned upper and lower limits even if the particular combination is not specifically listed.

Embodiments of the disclosed process and system involve the production of acetic acid by carbonylating methanol in a carbonylation reaction. The carbonylation reaction may be represented by: $CH_3OH+CO \rightarrow CH_3COOH$ Embodiments of the disclosed process include: (a) obtaining HI in an acetic acid production system; and (b) continuously introducing an additive into the system, wherein the additive and HI interact to form a complex. The following description elaborates upon the disclosed process.

Embodiments of the disclosed process generally include (a) obtaining HI in an acetic acid production system; and (b) continually introducing an additive into the system, wherein the additive and HI interact to form a complex. In this context, the term "continually" means introducing the additive sufficiently frequently and in metered amounts to bring about steady state HI scavenging operations. This will eliminate large swings in the efficiency of scavenging operations produced in conventional practice by occasional introduction of large amounts of additive. The following description shall elaborate upon the disclosed process in detail.

Acetic Acid Production

FIG. 1 is a schematic of an exemplary acetic acid production system 100 implementing the carbonylation reaction. In some embodiments, the acetic acid system 100 may include a reaction area 102, a light-ends area 104, a purification area 106, and recycle area 108. The reaction area 102 may include a reactor 110, a flash vessel 120, and associated equipment. The reactor 110 is a reactor or vessel in which methanol is carbonylated in the presence of a catalyst to form acetic acid at elevated pressure and temperature. Note that the "streams" discussed herein may be part of more than one functional area.

The reaction area 102 may comprise a reactor 110, a flash vessel 120, equipment associated with the reactor 110 and flash vessel 120, and streams associated with the reactor 110 and flash vessel 120. For example, the reaction area 102 may comprise reactor 110, flash vessel 120, and streams (or portions of streams) 111, 112, 114, 121, 126, 131, 160, 138, 139, 148. The reactor 110 is a reactor or vessel in which methanol is carbonylated in the presence of a catalyst to form acetic acid at elevated pressure and temperature. The flash vessel 120 is a tank or vessel in which a reaction mixture obtained in the reactor, for example the reactor 110, is at least partially depressurized and/or cooled to form a vapor stream and a liquid stream. A vapor stream is a product or composition which comprises components in the gaseous state under the conditions of the processing step in which the stream is formed. A liquid stream may be a product or composition which comprises components in the liquid state under the conditions of the processing step in which the stream is formed.

The light-ends area 104 may comprise a separations column, for example a light-ends column 130, equipment associated with light-ends column 130, and streams associated with the light-ends column 130. For example, the light-ends area 104 may comprise light-ends column 130, decanter 134, and streams 126, 131, 132, 133, 135, 136, 138, 139, 160. The light-ends column 130 is a fractioning or distillation column and includes any equipment associated with the column, including but not limited to heat exchangers, decanters, pumps, compressors, valves, and the like.

The purification area 106 may comprise a drying column 140, optionally, a heavy-ends column 150, equipment associated with drying column 140 and heavy-ends column 150, and streams associated with the drying column 140 and heavy-ends column 150. For example, the purification area 106 may comprise drying column 140, heavy-ends column 150, and streams 136, 141, 142, 145, 148, 151, 152, 156. The heavy-ends column 150 is a fractioning or distillation column and includes any equipment associated with the column, including but not limited to heat exchangers, decanters, pumps, compressors, valves, and the like.

The recycle area 108 may comprise process streams recycled to the reaction area 102 and/or light-ends area 104. For example, in FIG. 1, the recycle area 108 may comprise streams 121, 138, 139, 148.

In an embodiment, the reactor 110 may be configured to receive a carbon monoxide feed stream 114 and a methanol feed stream 112. The feed stream 112 may comprise a methanol feed stream, a methyl acetate feed stream or any mixture of the two. In the illustrated embodiment, the feed stream 112 is a mixed stream. A reaction mixture may be withdrawn from the reactor in stream 111. Other streams may be included such as, for example, a stream that may recycle a bottoms mixture of the reactor 110 back into the reactor 110, or a stream may be included to release a gas from the reactor 110. Stream 111 may comprise at least a part of the reaction mixture.

In an embodiment, the flash vessel 120 may be configured to receive stream 111 from the reactor 110. In the flash vessel 120, stream 111 may be separated into a vapor stream 126 and a liquid stream 121. The vapor stream 126 may be communicated to the light-ends column 130, and the liquid stream 121 may be communicated to the reactor 110. In an embodiment, stream 126 may have acetic acid, water, methyl iodide, methyl acetate, HI, mixtures thereof.

In an embodiment, the light-ends column 130 may be a distillation column and associated equipment such as a decanter 134, pumps, compressors, valves, and other related equipment. The light-ends column 130 may be configured to receive stream 126 from the flash vessel 120. In the illustrated embodiment, stream 132 is the overhead product from the light-ends column 130, and stream 131 is bottoms product from the light-ends column 130. As indicated, light-ends column 130 may include a decanter 134, and stream 132 may pass into decanter 134.

Stream 135 may emit from decanter 134 and recycle back to the light-ends column 130. Stream 138 may emit from decanter 134 and may recycle back to the reactor 110 via, for example, stream 112 or be combined with any of the other streams that feed the reactor. Stream 139 may recycle a portion of the light phase of decanter 134 back to the reactor 110 via, for example, stream 112. Stream 136 may emit from the light-ends column 130. Other streams may be included such as, for example, a stream that may recycle a bottoms mixture of the light-ends column 130 back into the light-ends column 130. Streams received by or emitted from the light-ends column 130 may pass through a pump, compressor, heat exchanger, and the like as is common in the art.

In an embodiment, the drying column 140 may be a vessel and associated equipment such as heat exchangers, decanters, pumps, compressors, valves, and the like. The drying column 140 may be configured to receive stream 136 from the light-ends column 130. The drying column 140 may separate components of stream 136 into streams 142 and 141.

Stream 142 may emit from the drying column 140, recycle back to the drying column via stream 145, and/or recycle back to the reactor 110 through stream 148 (via, for example, stream 112). Stream 141 may emit from the drying column 140 and may include de-watered crude acetic acid product. Stream 142 may pass through equipment such as, for example, a heat exchanger or separation vessel before streams 145 or 148 recycle components of stream 142. Other streams may be included such as, for example, a stream may recycle a bottoms mixture of the drying column 140 back into the drying column 140. Streams received by or emitted from the drying column 140 may pass through a pump, compressor, heat exchanger, separation vessel, and the like as is common in the art.

The heavy-ends column 150 may be a distillation column and associated equipment such as heat exchangers, decanters, pumps, compressors, valves, and the like. The heavy-ends column 150 may be configured to receive stream 141 from the drying column 140. The heavy-ends column 150 may separate components from stream 141 into streams 151, 152, and 156. Streams 151 and 152 may be sent to additional processing equipment (not shown) for further processing. Stream 152 may also be recycled, for example, to light-ends column 130. Stream 156 may have acetic acid product.

A single column (not depicted) may be used in the place of the combination of the light-ends distillation column 130 and the drying column 140. The single column may vary in the diameter/height ratio and the number of stages according to the composition of vapor stream from the flash separation and the requisite product quality. For instance, U.S. Pat. No. 5,416,237, the teachings of which are incorporated herein by reference, discloses a single column distillation.

Alternative embodiments for the acetic acid production system 100 may also be found in U.S. Pat. Nos. 6,552,221, 7,524,988, and 8,076,512, which are fully incorporated herein by reference.

In an embodiment, the carbonylation reaction in reactor 110 of system 100 may be performed in the presence of a catalyst. Catalysts may include, for example, rhodium catalysts and iridium catalysts.

Suitable rhodium catalysts are taught, for example, by U.S. Pat. No. 5,817,869, which is herein incorporated by reference. The rhodium catalysts may include rhodium metal and rhodium compounds. In an embodiment, the rhodium compounds may be selected from the group consisting of rhodium salts, rhodium oxides, rhodium acetates, organo-rhodium compounds, coordination compounds of rhodium, the like, and mixtures thereof in an embodiment, the rhodium compounds may be selected from the group consisting of $Rh_2(CO)+I_2$, $Rh_2(CO)+Br_2$, $Rh_2(CO)+C_{12}$, $Rh(CH_3CO_2)_2$, $Rh(CH_3CO_2)_3$, $[H]Rh(CO)_2I_2$, the like, and mixtures thereof. In an embodiment, the rhodium compounds may be selected from the group consisting of $[H]Rh(CO)_2I_2$, $Rh(CH_3CO_2)_2$, the like, and mixtures thereof.

Suitable iridium catalysts are taught, for example, by U.S. Pat. No. 5,932,764. The iridium catalysts may include iridium metal and iridium compounds. Examples of suitable iridium compounds include $IrCl_3$, $IrI_3$, $IrBr_3$, $[Ir(CO)_2I]_2$, $[Ir(CO)_2Cl]_2$, $[Ir(CO)_2Br]_2$, $[Ir(CO)4I_2]$—H+, $[Ir(CO)_2Br_2]$—H+, $[IR(CO)_2I_2]$—H+, $[Ir(CH_3)I_3(CO)_2]$—H+, $Ir_4(CO)_{12}$, $IrCl_3 \cdot 4H_2O$, $IrBr_3 \cdot 4H_2O$, $Ir_3(CO)I_2$, $Ir_{203}$, $IrO_2$, $Ir(acac)(CO)_2$, $Ir(acac)_3$, $Ir(OAc)_3$, $[Ir_3O(OAc)_6(H_2O)_3][OAc]$, $H_2[IrCl_6]$, the like, and mixtures thereof. In an embodiment, the iridium compounds may be selected from the group consisting of acetates, oxalates, acetoacetates, the like, and mixtures thereof. In an embodiment, the iridium compounds may be one or more acetates.

In an embodiment, the catalyst may be used with a co-catalyst. In an embodiment, co-catalysts may include metals and metal compounds selected from the group consisting of osmium, rhenium, ruthenium, cadmium, mercury, zinc, gallium, indium, and tungsten, their compounds, the like, and mixtures thereof. In an embodiment, co-catalysts may be selected from the group consisting of ruthenium compounds and osmium compounds. In an embodiment, co-catalysts may be one or more ruthenium compounds. In an embodiment, the co-catalysts may be one or more acetates.

The reaction rate depends upon the concentration of the catalyst in the reaction mixture in reactor 110. In an embodiment, the catalyst concentration may be in a range from about 1.0 mmol to about 100 mmol catalyst per liter (mmol/l) of reaction mixture. In some embodiments the catalyst concentration is at least 2.0 mmol/l, or at least 5.0 mmol/l, or at least 7.5 mmol/l. In some embodiments the catalyst concentration is at most 75 mmol/l, or at most 50 mmol/l, or at most 25 mmol/l. In particular embodiments, the catalyst concentration is from about 2.0 to about 75 mmol/l, or from about 5.0 to about 50 mmol/l, or from about 7.5 to about 25 mmol/l.

In an embodiment, the carbonylation reaction in reactor 110 of system 100 may be performed in the presence of a catalyst stabilizer. Suitable catalyst stabilizers include at least two types of catalyst stabilizers. The first type of catalyst stabilizer may be a metal iodide salt such as lithium iodide. The second type of catalyst stabilizer may be a non-salt stabilizer. In an embodiment, non-salt stabilizers may be pentavalent Group 15 oxides, such as that disclosed in U.S. Pat. No. 9,790,159, which is herein incorporated by reference. In an embodiment, the catalyst stabilizer may be one or more phosphine oxides. In an embodiment, the catalyst stabilizer may be CYTOP™ 503 from Solvay.

The additive disclosed herein is a pentavalent Group 15 oxide. The pentavalent Group 15 oxide is soluble in acetic acid and comprises a bidentate phosphine dioxide, a tertiary arsine oxide, or combination thereof.

In some embodiments, the bidentate phosphine dioxide can be represented by Formula I:

Formula I

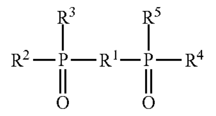

wherein:

P is phosphorous;

O is oxygen;

$R^1$ is selected from $C_1$-$C_{10}$ alkyls;

$R^2$, $R^3$, $R^4$, and $R^5$ are each independently selected from $C_4$-$C_{18}$ alkyls, $C_4$-$C_{18}$ aryls, $C_4$-$C_{18}$ cyclic alkyls, $C_4$-$C_{18}$ cyclic aryls, and combinations thereof, and can be the same as or different from one another; and each bidentate phosphine dioxide has at least 17 carbon atoms.

In further embodiments, $R^1$ is selected from $C_1$, $C_3$, $C_5$, $C_7$, and $C_9$ alkyl groups, and $R^2$, $R^3$, $R^4$, and $R^5$ are each independently selected from $C_4$-$C_{18}$ cyclic aryls.

Examples of suitable bidentate phosphine dioxide for use as a pentavalent Group 15 oxide include, but are not limited to, bis(diphenylphosphino)methane dioxide (bis-DPP-$MeO_2$), bis(diphenylphosphino)propane dioxide (bis-DPP-$PrO_2$), bis(diphenylphosphino)pentane dioxide (bis-$DPPPeO_2$), and combinations thereof.

In one or more embodiments, the bidentate phosphine dioxide exhibits a melting point of greater than 100° C., or greater than 200° C., or greater than 300° C., for example.

In one or more embodiments, the bidentate phosphine dioxide has a phosphoryl group frequency of less than or equal to 1190 $cm^{-1}$ in acetonitrile at 25° C. as measured by Fourier transform infrared spectroscopy.

In some embodiments, the tertiary arsine oxide can be represented by Formula II:

Formula II

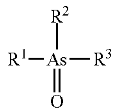

wherein:

As is arsenic;

O is oxygen; and $R^1$, $R^2$, and $R^3$ are each independently selected from $C_1$-$C_{10}$ alkyls, $C_4$-$C_{18}$ aryls, $C_4$-$C_{18}$ cyclic alkyls, $C_4$-$C_{18}$ cyclic aryls, and combinations thereof, and can be the same as or different from one another.

In further embodiments, $R^1$, $R^2$, and $R^3$ are each independently selected from $C_1$-$C_{10}$ alkyls, $C_4$-$C_{18}$ cyclic aryls, and combinations thereof.

Examples of suitable phosphine oxides for use as a pentavalent Group 15 oxide include, but are not limited to, triphenyl arsine oxide (TPAsO), triethylarsine oxide (TEtAsO), and combinations thereof.

In one or more embodiments, the tertiary arsine oxide exhibits a melting point of greater than 100° C., or greater than 200° C., or greater than 300° C.

In some embodiments, the tertiary arsine oxide has a $pK_{BHX}$ less than or equal to 5.00, a $\Delta G°$ less than or equal to −20 KJ $mol^{-1}$, or a combination thereof, wherein $pK_{BHX}$ and $\Delta G°$ are measure in $CCl_4$ at 25° C. Further discussion of $pK_{BHX}$ and $\Delta G°$ can be found in "Lewis Basicity and Affinity Scales", C. Laurence & J. Gal, Wiley ISBN 978-0-470-74957-9, 2010, the substance of which is incorporated herein by reference.

The amount of pentavalent Group 15 oxide, when used, is such that a molar ratio to carbonylation catalyst is greater than about 0.5:1. In some embodiments, the molar ratio of the pentavalent Group 15 oxide to rhodium is from about 0.5:1 to about 100:1. In some embodiments, from about 0.005 to about 2.0 M of the pentavalent Group 15 oxide may be in the reaction mixture. In some embodiments, from about 0.01 to about 1.5 M, or from 0.025 to 1.2 M, of the pentavalent Group 15 oxide may be in the reaction mixture.

In other embodiments, the reaction may occur in the absence of a stabilizer selected from the group of metal iodide salts and non-metal stabilizers such as pentavalent Group 15 oxides. In further embodiments, the catalyst stabilizer may consist of an additive which is brought into contact with the reaction mixture stream 111 in the flash vessel 120.

In an embodiment, hydrogen may also be fed into the reactor 110. Addition of hydrogen can enhance the carbonylation efficiency. In an embodiment, the concentration of hydrogen may be in a range of from about 0.1 mol % to about 5 mol % of carbon monoxide in the reactor 110. In an embodiment, the concentration of hydrogen may be in a range of from about 0.3 mol % to about 3 mol % of carbon monoxide in the reactor 110.

In an embodiment, the carbonylation reaction in reactor 110 of system 100 may be performed in the presence of water. In an embodiment, the concentration of water is from about 0.1 wt % to about 10.0 wt %, about 0.2 wt % to about 6.0 wt %, about 0.3 wt % to about 4.5 wt %, or about 0.4 wt % to about 2 wt %, based on the total weight of the reaction mixture.

In an embodiment, the carbonylation reaction may be performed in the presence of methyl acetate. Methyl acetate may be formed in situ. In embodiments, methyl acetate may be added as a starting material to the reaction mixture. In an embodiment, the concentration of methyl acetate may be from about 2 wt % to about 20 wt % based on the total weight of the reaction mixture. In an embodiment, the concentration of methyl acetate may be from about 2 wt % to about 16 wt %. In an embodiment, the concentration of methyl acetate may be from about 2 wt % to about 8 wt %. Alternatively, methyl acetate or a mixture of methyl acetate and methanol from byproduct streams of the methanolysis of polyvinyl acetate or ethylene-vinyl acetate copolymers can be used for the carbonylation reaction.

In an embodiment, the carbonylation reaction may be performed in the presence of methyl iodide. Methyl iodide may be a catalyst promoter. In an embodiment, the concentration of MeI may be from about 0.6 wt % to about 36 wt % based on the total weight of the reaction mixture. In an embodiment, the concentration of MeI may be from about 4 wt % to about 24 wt %. In an embodiment, the concentration of MeI may be from about 6 wt % to about 20 wt %. Alternatively, MeI may be generated in the reactor 110 by adding HI.

In an embodiment, methanol and carbon monoxide may be fed to the reactor 110 in stream 112 and stream 114, respectively. The methanol feed stream to the reactor 110 may come from a syngas-methanol facility or any other source. Methanol does not react directly with carbon monoxide to form acetic acid. It is converted to MeI by the HI present in the reactor 110 and then reacts with carbon monoxide and water to give acetic acid and regenerate the HI.

In an embodiment, the carbonylation reaction in reactor 110 of system 100 may occur at a temperature within the range of about 120° C. to about 250° C., alternatively, about 150° C. to about 250° C., alternatively, about 150° C. to about 200° C. In an embodiment, the carbonylation reaction in reactor 110 of system 100 may be performed under a pressure within the range of about 200 psia (1.38 MPa-a) to 2,000 psia (13.8 MPa-a), alternatively, about 200 psia (1.38 MPa-a) to about 1,000 psia (6.9 MPa-a), alternatively, about 300 psia (2.1 MPa-a) to about 500 psia (3.4 MPa-a).

In an embodiment, the reaction mixture may be withdrawn from the reactor 110 through stream 111 and is flashed in flash vessel 120 to form a vapor stream 126 and a liquid stream 121. The reaction mixture in stream 111 may include acetic acid, methanol, methyl acetate, methyl iodide, carbon monoxide, carbon dioxide, water, HI, heavy impurities, catalyst, or combinations thereof. The flash vessel 120 may comprise any configuration for separating vapor and liquid components via a reduction in pressure. For example, the flash vessel 120 may comprise a flash tank, nozzle, valve, or combinations thereof.

The flash vessel 120 may have a pressure below that of the reactor 110. In an embodiment, the flash vessel 120 may have a pressure of from about 10 psig (69 kPa-g) to 100 psig (689 kPa-g). In an embodiment, the flash vessel 120 may have a temperature of from about 100° C. to 160° C.

The vapor stream 126 may include acetic acid and other volatile components such as methanol, methyl acetate, methyl iodide, carbon monoxide, carbon dioxide, water, entrained HI, complexed HI, and mixtures thereof. The liquid stream 121 may include acetic acid, methanol, methyl acetate, methyl iodide, carbon monoxide, carbon dioxide, water, complexed HI, HI, an azeotrope of HI and water, and mixtures thereof. In particular, it may comprise the catalyst, complexed HI, HI, an azeotrope of HI and water, and mixtures thereof. The liquid stream 121 may further comprise sufficient amounts of water and acetic acid to carry and stabilize the catalyst, non-volatile catalyst stabilizers, or combinations thereof. The liquid stream 121 may recycle to the reactor 110. The vapor stream 126 may be communicated to light-ends column 130 for distillation.

In an embodiment, the vapor stream 126 may be distilled in a light-ends column 130 to form an overhead stream 132, a crude acetic acid product stream 136, and a bottom stream 131. In an embodiment, the light-ends column 130 may have at least 10 theoretical stages or 16 actual stages. In an alternative embodiment, the light-ends column 130 may have at least 14 theoretical stages. In an alternative embodiment, the light-ends column 130 may have at least 18 theoretical stages. In embodiments, one actual stage may equal approximately 0.6 theoretical stages. Actual stages can be trays or packing. The reaction mixture may be fed via stream 126 to the light-ends column 130 at the bottom or the first stage of the column 130.

Stream 132 may include acetaldehyde, water, carbon monoxide, carbon dioxide, methyl iodide, methyl acetate, methanol and acetic acid, additive, and mixtures thereof. Stream 131 may have acetic acid, methyl iodide, methyl acetate, HI, water, and mixtures thereof. Stream 136 may have acetic acid, HI, water, heavy impurities, and mixtures thereof. Streams 132, 131, and 136, as well as other streams discussed herein, may also comprise additive at varying concentrations, depending on where the additive is added to the system.

In an embodiment, the light-ends column 130 may be operated at an overhead pressure within the range of 20 psia (138 kPa-a) to 40 psia (276 kPa-a), alternatively, the overhead pressure may be within the range of 30 psia (207 kPa-a) to 35 psia (241 kPa-a). In an embodiment, the overhead temperature may be within the range of 95° C. to 135° C., alternatively, the overhead temperature may be within the range of 110° C. to 135° C., alternatively, the overhead temperature may be within the range of 125° C. to 135° C. In an embodiment, the light-ends column 130 may be operated at a bottom pressure within the range of 25 psia (172 kPa-a) to 45 psia (310 kPa-a), alternatively, the bottom pressure may be within the range of 30 psia (207 kPa-a) to 40 psia (276 kPa-a).

In an embodiment, the bottom temperature of the light-ends column 130 may be within the range of 115° C. to 155° C., alternatively, the bottom temperature is within the range of 125° C. to 135° C. In an embodiment, crude acetic acid in stream 136 may be emitted from the light-ends column 130 as a liquid side-draw. Stream 136 may be operated at a pressure within the range of 25 psia (172 kPa-a) to 45 psia (310 kPa-a), alternatively, the pressure may be within the range of 30 psia (207 kPa-a) to 40 psia (276 kPa-a). In an embodiment, the temperature of stream 136 may be within the range of 110° C. to 140° C., alternatively, the temperature may be within the range of 125° C. to 135° C. Stream 136 may be taken between the fifth to the eighth actual stage of the light-ends column 130.

The overhead vapor in stream 132 from the light-ends column 130 may be condensed and separated in a decanter 134 to form a light, aqueous phase and a heavy, organic phase. The heavy, organic phase may be recycled to the reactor 110 in stream 138 via stream 112, for example. The stream 138 may comprise acetic acid, methanol, methyl acetate, methyl iodide, carbon monoxide, carbon dioxide, water, HI, heavy impurities, an additive (optionally), and mixtures thereof.

The light, aqueous phase may be recycled to the light-ends column 130 in stream 135 or may be recycled to the reactor 110 in stream 139 via stream 112, for example. The stream 135 may comprise acetic acid, methanol, methyl acetate, methyl iodide, carbon monoxide, carbon dioxide, water, HI, heavy impurities, an additive (optionally), and mixtures thereof. The heavy, organic phase in stream 138 may comprise methyl iodide, and methyl acetate, and mixtures thereof. The light, aqueous phase in streams 136 and 139 may comprise water (greater than 50%), acetic acid, comprise methanol, methyl acetate, methyl iodide, carbon monoxide, carbon dioxide, heavy impurities, an additive (optionally), and mixtures thereof. Make-up water may be introduced into the decanter 134 via stream 133. Streams 139 and 138 may be considered to be in the light-ends area 104 and the recycle area 108.

In one or more embodiments, the crude acetic acid in stream 136 may be optionally subjected to further purification, such as, but not limited to, drying-distillation, in drying column 140 to remove water and heavy-ends distillation in stream 141. Stream 141 may be communicated to heavy-ends column 150 where heavy impurities such as propionic acid may be removed in stream 151 and final acetic acid product may be recovered in stream 156.

In an embodiment, an additive may be continually introduced into the system 100 via stream 160. In FIG. 1, stream 160 mixes with the flash vessel 120 vapors to continually introduce the additive to the components of the flash vessel 120 vapor stream 126. In an alternative embodiment, stream 160 may continually introduce the additive into any equipment or streams in the reaction area 102, light-ends area 104, recycle area 108, or combinations thereof. For example, stream 160 may continually introduce the additive into the flash vessel 120, light-ends column 130, reactor 110, streams 111, 112, 114, 121, 126, 131, 132, 133, 135, 136, 138, 139, or combinations thereof. Therefore, although stream 160 is shown in FIG. 1 as mixing with the vapor stream emitted from the flash vessel 120, it is contemplated that alternative embodiments may include stream 160 as mixing with any equipment or stream in the reaction area 102, light-ends area 104, recycle area 108, or combinations thereof.

In some embodiments, the additive disclosed herein may be continually introduced in stream 160 as a solution. In an embodiment, the additive may be continually introduced in stream 160 as an additive solution comprising the additive and a solvent. In an embodiment, the additive solution may comprise an acetic acid solution. The nature of the solvent or diluent generally may not be critical so long as the solvent or diluent does not interfere with the carbonylation reaction or the purification of the acetic acid in the purification area 106.

Those skilled in the art of homogeneous processes having the benefit of this disclosure, and in particular those processes that require a flashing step to disengage in volatile catalysts and additives, will appreciate that attrition rates of catalysts and additives solely related to entrainment will be a function of several variables. Among these variables are reactor size feed rate, and flasher size and flashing rate. They will also appreciate that a make-up solution of the additive disclosed herein in acetic acid ("HAc") could be as concentrated as the solubility limit of the additive disclosed herein in HAc allows, which is about 50 wt % or as dilute as a few ppm.

A primary consideration is that the flow rate and concentration of the make-up stream comprising the additive disclosed herein are matched such that there is a steady state concentration of additive in the reactor. This can normally vary from its high and low point between batch additions of up to 1.5 wt %, is now controlled within a target range of preferably +/−0.5 wt % and most preferably +/−0.2 wt %. Thus, for example in a process with an attrition rate of 1 wt % per month from the reactor, a monthly batch addition could be replaced by a continually metered stream corresponding to an average daily addition of the additive disclosed herein of about 0.03 wt %"

In an embodiment, no solvent or diluent may be used. In an embodiment, the solvent or diluent is one or more of the liquid constituents of the reaction mixture in reactor 110, e.g., acetic acid, methanol, methyl iodide, water, or combinations thereof. In an embodiment, the solvent or dilution may be acetic acid, methanol, or both. Similarly, the amount of solvent or diluents used in this context is not critical and may be adjusted broadly depending on process economy. The use of a solvent or diluent may be advantageous to ensure fast and even distribution and contact of the additive with HI.

In an embodiment, when the additive is introduced to the system 100 separately and independently from the reaction mixture and from any recycle stream it may be advantageous to employ a solvent or diluent. Such a "recycle stream" may be a product or composition which is recovered from a processing step downstream of the flash vessel and which is recycled to the reactor, flash vessel, or light-ends column. In an alternative embodiment, when the additive is brought into contact with the reaction mixture in the flash vessel 120, for example, by adding it to stream 131 prior to introducing the stream 131 to the flash vessel 120, the additive may be introduced in substance, i.e., in undiluted form, as the liquid constituents of the stream 131 act as solvents or diluents.

In an embodiment, the additive may comprise a catalyst stabilizer. In an embodiment, the additive may comprise a bidentate phosphine dioxide, a tertiary arsine oxide, or combination thereof. In an embodiment, the additive may comprise a triphenylphosphine dioxide, a triphenyl arsine oxide, or combination thereof.

Without intending to be limited by theory, it is believed that the additive (e.g., a bidentate phosphine dioxide, a tertiary arsine oxide, or combination thereof) may interact with HI to form a complex, as is discussed in the examples below. A HI complex may reduce a concentration of HI in the purification area 106 for at least the following reasons: i) the additive (e.g., a bidentate phosphine dioxide, a tertiary arsine oxide, or combination thereof), may have a relatively high boiling point and therefore may be retained in the liquid stream 121 of the flash vessel 120 where it may inhibit or at least significantly reduce the tendency of HI to be entrained in the vapor stream 126; ii) the additive may, by forming a complex with HI, act as a scavenger of HI and reducing the amount of HI which may become entrained in the vapor stream 126 and subsequently passed to the light-ends area 104; and iii) even if an amount of a HI complex becomes entrained in the vapor stream 126 and passes to the light-ends area 104, the HI complex (which may have a relatively high boiling point) may be recovered in the bottom stream 131 of the light-ends column 130. Thus, forming an HI complex enables the system 100 to inhibit or at least reduce transport of HI into the purification area 106 by enhancing recovery of HI (as a HI complex) in the reaction area 102 (e.g., in the liquid stream 121 of the flash vessel 120) and in the light-ends area 104 (e.g., in the bottom stream 131 of the light-ends column 130).

Recovery of HI (as a HI complex) also may counter effects of HI volatilization in the case of azeotropic breakdown. Hydrogen iodide forms a high boiling azeotrope in acetic acid solutions having greater than about 5 wt % water. If the water concentration (e.g., in the stream 131) falls below about 5 wt %, azeotropic breakdown and HI volatilization may occur. Such volatilization may lead to less HI in the bottom stream 131 obtained in the light-ends column 130 and returned to the reactor 110, and thus, may adversely impact reactor iodide inventory.

Additionally, in the case of azeotropic breakdown, volatilized HI may become part of the stream 136 which is withdrawn from the light-ends column 130 for purification in the purification area 106. Because the additive (e.g., a bidentate phosphine dioxide, a tertiary arsine oxide, or combination thereof) forms a complex with HI, continually introducing an additive may act as a scavenger for the volatized HI in the event of azeotropic breakdown in the light-ends column 130 and may inhibit or at least reduce transfer of volatized HI into the purification area 106. Because some additives (e.g., a bidentate phosphine dioxide, a tertiary arsine oxide, or combination thereof) double as a catalyst stabilizer for carbonylation reactions in reactor 110, the reaction in reactor 110 experiences little detriment as a result of any HI complex recycled to reactor 110.

Without intending to be limited by theory, it is believed that continually introducing the additive (e.g., a bidentate phosphine dioxide, a tertiary arsine oxide, or combination thereof) into the process at different points in the reaction area 102 or light-ends area 104 of system 100 reduces the likelihood of HI transfer to the purification area 106.

In an embodiment, continually introducing an additive (e.g., a bidentate phosphine dioxide, a tertiary arsine oxide, or combination thereof) may comprise continually metering the additive in solution (e.g., an acetic acid solution) using a gas or liquid metering technology known in the art such as turbine meters, Coriolis meters, ultrasonic meters, PD meters, or combinations thereof. Continuously metering may comprise uniformly injecting a known concentration of additive in solution (e.g., an acetic acid solution).

The reaction of the additive with HI is rapid and is generally quantitative at a temperature of about 10° C. In embodiments, the reaction takes place when the additive is brought into contact with a process stream which is upstream of the heavy-ends distillation column.

In an embodiment, the reaction mixture in reactor 110 does not comprise additive) other than the additive continually introduced into the system 100 and which has been recycled to the reactor 110.

In an embodiment, the amount of additive which is brought into contact with the HI is generally not critical so long as the additive is provided in an effective amount. An effective amount in this context is the amount of additive which is capable of scavenging at least a part of the HI which is present at a point in the system 100. The amount of additive that is added is governed by the attrition rate of the additive from reactor rather than the HI concentration.

In an embodiment, the rate at which additive is introduced into the system 100 may be adjusted depending on the HI content. In some embodiments, the additive may be introduced in an amount of at least about 0.1 mol per mol HI. In alternative embodiments, at least about 0.5 mol additive, or at least about 1 mol additive, or at least about 1.5 mol additive, per mol HI is introduced. In alternative embodiments, the additive may be introduced in an amount of from about 0.1 to about 10 mol per mol HI. In alternative embodiments, the amount of additive is from about 0.25 to about 7.5 mol, or from about 0.5 to about 5 mol, or from about 0.75 to about 1.5 mol, per mol HI.

In further alternative embodiments, the amount of additive is from about 1 to about 10 mol, or from about 1 to about 7.5 mol, or from about 1 to about 5 mol, per mol HI. In alternative embodiments, the additive may be introduced in an amount from about 0.1 to about 1.5 mol per mol HI. In alternative embodiments, the amount of additive introduced may be from about 0.1 to about 1.3 mol, or from about 0.1 to about 1.1 mol, per mol HI. In further alternative embodiments, the amount of additive is from about 0.5 to about 3 mol, or from about 0.5 to about 2 mol, or from about 0.5 to about 1.5 mol, per mol HI.

Generally, it is not detrimental to the subsequent separation and purification of the final acetic acid product if the molar amount of additive exceeds the molar amount needed to complex HI, so long as the boiling point of the additive is sufficiently higher than the boiling point of the vapor stream 126 which emits from the flash vessel 120 and/or the stream 136 which emits from the light-ends column 130. For example, the boiling point of the additive is sufficiently higher when the boiling point is at least 15° C., alternatively, at least 30° C., or alternatively, at least 50° C. above the boiling point of the crude acetic acid in stream 136.

In particular variants, of these embodiments, the additive may be introduced in the flash vessel 120 in an amount from about 0.1 to about 1.5 mol per mol HI. In alternative variants, the amount of additive is from about 0.1 to about 1.3 mol, or from about 0.1 to about 1.1 mol, per mol HI. In further alternative embodiments, the amount of additive is from about 0.5 to about 3 mol, or from about 0.5 to about 2 mol, or from about 0.5 to about 1.5 mol, per mol HI.

In further embodiments, the additive may be introduced in the flash vessel 120 in an amount sufficient to establish a concentration of no more than about 20 wt % of the additive in the liquid stream 121. In alternative embodiments, the additive may be introduced to establish a concentration of no more than about 15 wt %, or no more than about 12 wt %, or no more than about 10 wt %, of the additive in the liquid stream 121. In other embodiments, the additive may be introduced in an amount sufficient to establish a concentration of at least about 0.5 wt % of the additive in the liquid stream 121. In alternative embodiments, the additive may be introduced in an amount sufficient to establish a concentration of at least about 1 wt %, or at least about 2.5 wt %, or at least about 4 wt %, of the additive in the liquid stream 121. In particular embodiments, the additive may be introduced in an amount sufficient to establish a concentration of from about 0.5 wt % to about 20 wt % of the additive in the liquid stream 121.

In alternative embodiments, the additive may be introduced in an amount sufficient to establish a concentration of from about 1 wt % to about 20 wt %, or from about 2.5 wt % to about 20 wt %, or from about 4 wt % to about 20 wt %, of the additive in the liquid stream 121. In alternative embodiments, the additive may be introduced in an amount sufficient to establish a concentration of from about 0.5 wt % to about 15 wt %, or from about 1 wt % to about 15 wt %, or from about 2.5 wt % to about 15 wt %, or from about 4 wt % to about 15 wt %, of the additive in the liquid stream 121. In alternative embodiments, the additive may be introduced in an amount sufficient to establish a concentration of from about 0.5 wt % to about 12 wt %, or from about 1 wt % to about 12 wt %, or from about 2.5 wt % to about 12 wt %, or from about 4 wt % to about 12 wt %, of the additive in the liquid stream 121.

The liquid stream 121 can be recycled to the reactor 110. The recycled liquid stream 121 may introduce the additive into the reactor 110, and consequently into the reaction mixture in reactor 110.

In some embodiments, the amount of the additive which is introduced in the flash vessel 120 may be adjusted to establish a steady state concentration of no more than about 20 wt % of the additive in the reaction mixture. In alternative embodiments, the additive may be introduced in the flash vessel 120 in an amount sufficient to establish a steady state concentration of no more than about 17 wt %, or no more than about 15 wt %, or no more than about 12 wt %, of the additive in the reaction mixture. In other embodiments, the additive may be introduced in the flash vessel 120 in an amount sufficient to establish a steady state concentration of at least about 2 wt % of the additive in the reaction mixture. In alternative embodiments, the additive may be introduced in the flash vessel 129 in an amount sufficient to establish a steady state concentration of at least about 5 wt %, or at least about 7 wt %, of the additive in the reaction mixture.

In particular embodiments, the additive may be introduced in the flash vessel 120 in an amount sufficient to establish a steady state concentration from about 2 wt % to about 20 wt % of the additive in the reaction mixture. In alternative embodiments, the additive may be introduced in the flash vessel 120 in an amount sufficient to establish a steady state concentration of from about 5 wt % to about 20 wt %, or from about 7 wt % to about 20 wt %, of the additive in the reaction mixture. In alternative embodiments, the additive may be introduced in the flash vessel 120 in an amount sufficient to establish a steady state concentration of from about 2 wt % to about 17 wt %, or from about 5 wt % to about 17 wt %, or from about 7 wt % to about 17 wt %, of the additive in the reaction mixture.

In alternative embodiments, the additive may be introduced in the flash vessel 120 in an amount sufficient to establish a steady state concentration of from about 2 wt % to about 15 wt %, or from about 5 wt % to about 15 wt %, or from about 7 wt % to about 15 wt %, of the additive in the reaction mixture. In alternative embodiments, the additive may be introduced in the flash vessel 120 in an amount sufficient to establish a steady state concentration of from about 2 wt % to about 12 wt %, or from about 5 wt % to about 12 wt %, or from about 7 wt % to about 12 wt %, of the additive in the reaction mixture.

In general, the additive may be introduced into the system 100 only continually. The process in accordance with the present disclosure differs from the prior procedures at least in that additive may be introduced into the system 100 downstream of reactor 110 and upstream of the purification area 106.

Despite efficient complexation, residual HI which may reach the light-ends column 130 may be easily separated from as a bottom product stream 131 of the light-ends area 104. Also, due to the removal of HI from the product stream in the earliest stage of the acetic acid work-up, side reactions which are caused by HI, i.e., the formation of undesirable long chain alkyl iodide contaminants in the product stream downstream from the flash vessel, are significantly reduced. Additionally, the reduced amounts of HI in the product streams downstream from the flash vessel 120 alleviate corrosion and engineering problems. Also, the additive acts as a catalyst stabilizer. Therefore, problems caused by losses of catalyst due to deactivation or deposition are reduced or may even be avoided.

The beneficial effect of the additive on the vaporization of HI is not restricted to the point of introduction into the system 100. Rather, as the additive circulates in the system 100 by recycling the liquid stream 121 from the flash vessel 120 to the reactor 110, its presence in the reaction mixture aids in reducing the tendency of HI to vaporize in the flash vessel 120, thus aiding in reducing the amount of HI which may become entrained in the vapor stream 126. Therefore, upon continuous operation of the process, the amount of additive which is brought into contact with the reaction mixture in the flash vessel 120 normally may be decreased as steady state conditions are achieved. Under steady state conditions, the amount of additive which is brought into contact with the reaction mixture in the flash vessel 120 normally can be reduced to amounts necessary to maintain the desired steady state concentration of the additive.

CERTAIN EMBODIMENTS

In some embodiments, a process for producing acetic acid in an acetic acid production system, comprises contacting methanol and carbon monoxide in the presence of a liquid reaction medium comprising iodide under carbonylation conditions sufficient to form acetic acid. The liquid reaction medium comprises a carbonylation catalyst, water, and an additive. The carbonylation catalyst is selected from the group consisting of rhodium catalysts, iridium catalysts and palladium catalysts. The water is present in the liquid reaction medium in the range of from 0.1 wt % to 10 wt %, based on the weight of the liquid reaction medium. The additive is present in the liquid reaction medium at an additive to iodide molar ratio of about 0.005 to about 2.0 M, along with in-situ generated derivatives of the additive, and/or combinations thereof. The additive comprises a bidentate phosphine dioxide, a tertiary arsine oxide, or a combination thereof. The process further comprises recovering the acetic acid.

In further embodiments of the process for producing acetic acid in an acetic acid production system, the method is further characterized by one or more of the following:

a) the additive is continually added as an acetic acid solution;

b) the bidentate phosphine dioxide can be represented by Formula I:

Formula I

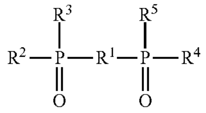

wherein:

P is phosphorous;

O is oxygen;

$R^1$ is selected from $C_1$-$C_{10}$ alkyls;

$R^2$, $R^3$, $R^4$, and $R^5$ are each independently selected from $C_4$-$C_{18}$ alkyls, $C_4$-$C_{18}$ aryls, $C_4$-$C_{18}$ cyclic alkyls, $C_4$-$C_{18}$ cyclic aryls, and combinations thereof, and can be the same as or different from one another; and each bidentate phosphine dioxide has at least 17 carbon atoms; or.

c) the bidentate phosphine dioxide is selected from bis(diphenylphosphino)methane dioxide (bis-DPPMe$O_2$), bis(diphenylphosphino)propane dioxide (bis-DPPPr$O_2$), bis(diphenylphosphino)pentane dioxide (bis-DPPPe$O_2$), and combinations thereof;

d) the bidentate phosphine dioxide has a phosphoryl group frequency of less than or equal to 1190 $cm^{-1}$ in acetonitrile at 25° C. as measured by Fourier transform infrared spectroscopy;

e) the tertiary arsine oxide can be represented by Formula II:

Formula II

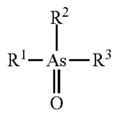

wherein:

As is arsenic;

O is oxygen; and $R^1$, $R^2$, and $R^3$ are each independently selected from $C_1$-$C_{10}$ alkyls, $C_4$-$C_{18}$ aryls, $C_4$-$C_{18}$ cyclic alkyls, $C_4$-$C_{18}$ cyclic aryls, and combinations thereof, and can be the same as or different from one another.

f) the tertiary arsine oxide is selected from triphenyl arsine oxide (TPAsO), triethylarsine oxide (TEtAsO), and combinations thereof;

g) the tertiary arsine oxide has a $pK_{BHX}$ less than or equal to 5.00, a $\Delta G°$ less than or equal to −20 KJ $mol^{-1}$, or a combination thereof, wherein $pK_{BHX}$ and $\Delta G°$ are measure in $CCl_4$ at 25° C.;

h) the additive exhibits a melting point of greater than 100° C., or greater than 200° C., or greater than 300° C.;

i) a molar ratio of the additive to the carbonylation catalyst is greater than about 0.5:1 or is in the range of from 0.5:1 to 100:1;

j) the liquid reaction medium comprises water in the range of from 0.1 wt % to 10 wt %, based on the weight of the liquid reaction medium;

k) the liquid reaction medium comprises a concentration of additive of about 0.01 to about 1.5 M, or from 0.025 to 1.2 M;

l) the process further comprises introducing a second concentration of the one or more additives into the process downstream of a reaction zone and, in some instances, adjusting the second concentration in response to a downstream iodide content;

m) the second concentration comprises a molar ratio of additive to iodide of 0.05:1 to 2.0:1;

n) the acetic acid is glacial acetic acid;

o) the carbonylation conditions comprise a temperature in a range of 150° C. to 250° C. and a pressure in a range of 200 psig (1,380 kPag) to 2,000 psig (1,380 MPag);

p) the acetic acid production system comprises a reaction area, a purification area, a light-ends area, a recycle area, and the additive is introduced upstream of the purification area;

q) the acetic acid production system comprises a drying column, the process further comprising continually introducing the additive upstream of the drying column;

r) the acetic acid production system comprises a reactor, the process further comprising continually introducing the additive into the reactor;

s) the acetic acid production system comprises a reactor and a stream in fluid communication with the reactor, the process further comprising continually introducing the additive into the stream;

t) the acetic acid production system comprises a flash vessel, the process further comprising continually introducing the additive into the flash vessel;

u) the acetic acid production system comprises a flash vessel and a stream in fluid communication with the flash vessel, the process further comprising continually introducing the additive into the stream;

v) the acetic acid production system comprises a light-ends column, the process further comprising continually introducing the additive into the light-ends column;

w) the acetic acid production system comprises a light-ends column and a stream in fluid communication with the light-ends column, the process further comprising continually introducing the additive into the stream;

x) the acetic acid production system comprises a drying column, the process further comprising continually introducing the additive into the drying column;

y) the acetic acid production system comprises a drying column and a stream in fluid communication with the drying column, the process further comprising continually introducing the additive into the stream;

z) the acetic acid production system comprises a recycle stream, the process further comprising continually introducing the additive into the recycle stream; and aa) the additive is introduced into the system in an amount based upon a rate of attrition of the additive from a reactor in the system.

In some embodiments, a method for reducing water in an acetic acid production process comprises contacting methanol and carbon monoxide in the presence of a liquid reaction medium comprising a first amount of hydrogen iodide, under carbonylation conditions sufficient to form acetic acid. The liquid reaction medium comprises a carbonylation catalyst, selected from the group consisting of rhodium catalysts, iridium catalysts and palladium catalysts and a first amount of water, sufficient to form an azeotropic mixture of the first amount of hydrogen iodide and the first amount of water. The method further comprises adding an additive to the liquid reaction medium at an additive to iodide molar ratio of about 0.005 to about 2.0 M, wherein the additive forms a complex with at least a portion of the first amount of hydrogen iodide resulting in a second amount of hydrogen iodide. The additive comprises a bidentate phosphine dioxide, a tertiary arsine oxide, or a combination thereof. The method further comprises reducing the water in the liquid reaction medium to a second amount of water while maintaining an azeotropic mixture of the second amount of hydrogen iodide and the second amount of water.

In further embodiments of the method for reducing water in an acetic acid production process, the method is further characterized by one or more of the following:

a) the additive is continually added as an acetic acid solution;

b) the bidentate phosphine dioxide can be represented by Formula I:

Formula I

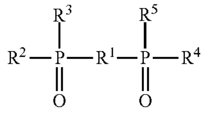

wherein:

P is phosphorous;

O is oxygen;

$R^1$ is selected from $C_1$-$C_{10}$ alkyls;

$R^2$, $R^3$, $R^4$, and $R^5$ are each independently selected from $C_4$-$C_{18}$ alkyls, $C_4$-$C_{18}$ aryls, $C_4$-$C_{18}$ cyclic alkyls, $C_4$-$C_{18}$ cyclic aryls, and combinations thereof, and can be the same as or different from one another; and each bidentate phosphine dioxide has at least 17 carbon atoms; or.

c) the bidentate phosphine dioxide is selected from bis(diphenylphosphino)methane dioxide (bis-$DPPMeO_2$), bis(diphenylphosphino)propane dioxide (bis-$DPPPrO_2$), bis(diphenylphosphino)pentane dioxide (bis-$DPPPeO_2$), and combinations thereof;

d) the bidentate phosphine dioxide has a phosphoryl group frequency of less than or equal to 1190 $cm^{-1}$ in acetonitrile at 25° C. as measured by Fourier transform infrared spectroscopy;

e) the tertiary arsine oxide can be represented by Formula II:

Formula II

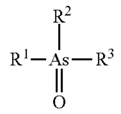

wherein:

As is arsenic;

O is oxygen; and $R^1$, $R^2$, and $R^3$ are each independently selected from $C_1$-$C_{10}$ alkyls, $C_4$-$C_{18}$ aryls, $C_4$-$C_{18}$ cyclic alkyls, $C_4$-$C_{18}$ cyclic aryls, and combinations thereof, and can be the same as or different from one another.

f) the tertiary arsine oxide is selected from triphenyl arsine oxide (TPAsO), triethylarsine oxide (TEtAsO), and combinations thereof;

g) the tertiary arsine oxide has a $pK_{BHX}$ less than or equal to 5.00, a $\Delta G°$ less than or equal to −20 KJ $mol^{-1}$, or a combination thereof, wherein $pK_{BHX}$ and $\Delta G°$ are measure in $CCl_4$ at 25° C.;

h) the additive exhibits a melting point of greater than 100° C., or greater than 200° C., or greater than 300° C.;

i) a molar ratio of the additive to the carbonylation catalyst is greater than about 0.5:1 or is in the range of from 0.5:1 to 100:1;

j) the liquid reaction medium comprises water in the range of from 0.1 wt % to 10 wt %, based on the weight of the liquid reaction medium;

k) the liquid reaction medium comprises a concentration of additive of in the range of from about 0.01 to about 1.5 M or from 0.025 to 1.2 M;

l) the process further comprises introducing a second concentration of the one or more additives into the process downstream of a reaction zone and, in some instances, adjusting the second concentration in response to a downstream iodide content;

m) the second concentration comprises a molar ratio of additive to iodide of 0.05:1 to 2.0:1;

n) the acetic acid is glacial acetic acid;

o) the carbonylation conditions comprise a temperature in a range of 150° C. to 250° C. and a pressure in a range of 200 psig (1,380 kPag) to 2,000 psig (1,380 MPag);

p) the acetic acid production system comprises a reaction area, a purification area, a light-ends area, a recycle area, and the additive is introduced upstream of the purification area;

q) the acetic acid production system comprises a drying column, the process further comprising continually introducing the additive upstream of the drying column;

r) the acetic acid production system comprises a reactor, the process further comprising continually introducing the additive into the reactor;

s) the acetic acid production system comprises a reactor and a stream in fluid communication with the reactor, the process further comprising continually introducing the additive into the stream;

t) the acetic acid production system comprises a flash vessel, the process further comprising continually introducing the additive into the flash vessel;

u) the acetic acid production system comprises a flash vessel and a stream in fluid communication with the flash vessel, the process further comprising continually introducing the additive into the stream;

v) the acetic acid production system comprises a light-ends column, the process further comprising continually introducing the additive into the light-ends column;

w) the acetic acid production system comprises a light-ends column and a stream in fluid communication with the light-ends column, the process further comprising continually introducing the additive into the stream;

x) the acetic acid production system comprises a drying column, the process further comprising continually introducing the additive into the drying column;

y) the acetic acid production system comprises a drying column and a stream in fluid communication with the drying column, the process further comprising continually introducing the additive into the stream;

z) the acetic acid production system comprises a recycle stream, the process further comprising continually introducing the additive into the recycle stream; and aa) the additive is introduced into the system in an amount based upon a rate of attrition of the additive from a reactor in the system.

Although the disclosed process and system have been described in detail, it should be understood that various changes, substitutions and alterations can be made herein without departing from the spirit and scope of the invention as defined by the appended claims. Moreover, the scope of the present application is not intended to be limited to the particular embodiments of the processes, machines, compositions, means, methods, and/or steps described in the specification. As one of the ordinary skill in the art will readily appreciate from the present disclosure, processes, machines, compositions, means, methods, and/or steps, presently existing or later to be developed that perform substantially the same function or achieve substantially the same result as the corresponding embodiments described herein, may be utilized according to the present invention. Accordingly, the appended claims are intended to include within their scope such processes, machines, compositions, means, methods, and/or steps.

EXAMPLES

The following investigations and examples are intended to be illustrative only, and are not intended to be, nor should they be construed as, limiting the scope of the present invention in any way.

Previously developed additives permitting a reduction in water content of the liquid reaction medium, comprising a carbonylation catalyst and hydrogen iodide, for production of acetic acid include phosphine oxides and compound mixtures of phosphine oxides. Such phosphine oxides (e.g., triphenylphosphine oxide), are described in U.S. Pat. Nos. 6,031,129 and 9,102,612, the teachings of which are fully incorporated herein by reference. Such phosphine oxides are exemplified hereinafter as triphenylphosphine oxide (TPPO). Such compound mixtures of phosphine oxides (e.g., a compound mixture of at least four phosphine oxides and pentavalent aryl or alkaryl phosphine oxides including one or more benzoyl groups), are described in U.S. Pat. Nos. 9,475,746 and 10,067,113, the teachings of which are fully incorporated herein by reference. Such compound mixtures of phosphine oxides are exemplified as Cyanex™ 923, formerly available from Cytec Corporation and now available from Solvay as CYTOP™ 503, and referred to hereinafter as compound mixture of phosphine oxides (CMPO).

Bidentate Phosphine Dioxides

Experiments were performed to explore a possible chelate effect of various bidentate phosphine oxides. These investigations involved spectroscopic studies at room temperature and vapor-liquid equilibrium (VLE) studies in which the extent of volatilization of HI into the vapor phase was determined by measurement of the iodide concentration in condensed vapor phase samples. As no bidentate phosphine oxides are commercially available, they were synthesized in-house via the reaction as shown below for bis(diphenylphosphino)ethane dioxide:

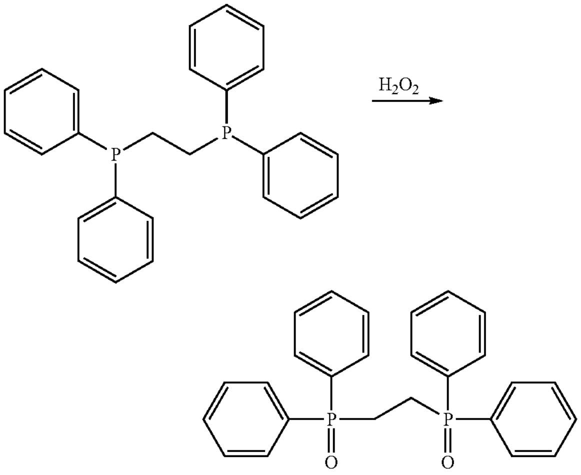

Bidentate Phosphine Dioxides

A two-fold molar excess of 30% aqueous $H_2O_2$ solution was added to the appropriate mass of the bidentate phosphine dissolved in either acetonitrile or glacial acetic acid (GAA). Quantitative formation of the dioxide was confirmed by FTIR in the acetonitrile solutions where the formed phosphoryl (P═O) peak is not masked by solvent peaks. Quantitative formation of the dioxide in GAA is assumed by virtue of heat liberated upon addition of the peroxide similar to in acetonitrile. Determination of P═O FTIR frequencies in acetonitrile as shown in the following Table 1, below, allows a gauge of basicity as lower frequency is associated with higher basicity. Further discussion of P—O bonds and basicity can be found in "The Effect of Complex Formation by Phosphine Oxides on Their P—O Stretching Frequencies," J Chem Soc, 2199-2203, 1960 and "Infrared and Raman Studies of Hydrogen Bonding in Organophosphorus Compounds-Proton Donors", Can J Spectroscopy, 32, 5 107-114, 1987, the disclosures of which are incorporated herein by reference.

It should be noted that somewhat surprisingly, in the bis(diphenylphosphino) series, only those with an odd numbered carbon chain length were soluble. Thus, bis(diphenylphosphino)ethane, bis(diphenylphosphino)butane, and bis(diphenylphosphino)hexane, were all insoluble and are not further reported on.

TABLE 1

| $R_3PO$ | $R_3PO$ | P═O, $cm^{-1}$ |
|---|---|---|
| Bis-DPPMe$O_2$ | Bis-DPPMe$O_2$ | 1,197.7 |
| TPPO | TPPO | 1,191.6 |
| Bis-DPPPr$O_2$ | Bis-DPPPr$O_2$ | 1,180.8 |
| Bis-DPPPrO | Bis-DPPPrO | 1,180.0 |
| Bis-DPPPe$O_2$ | Bis-DPPPe$O_2$ | 1,178.2 |
| Bis-DMePEt$O_2$ | Bis-DMePEt$O_2$ | 1,168.6 |
| Bis-DiCyPMe$O_2$ | Bis-DiCyPMe$O_2$ | 1,160.1 |
| Bis-DiCyPPR$O_2$ | Bis-DiCyPPR$O_2$ | 1,145.9 |
| CMPO | CMPO | 1,144.8 |
| $Ph_3AsO$ | $Ph_3AsO$ | 885.5 |

These data indicate that bis(diphenylphosphino)methane dioxide (bis-DPPMe$O_2$) is less basic than the longer chain propyl and pentyl analogs (DPPPr$O_2$ and DPPPe$O_2$) and all three are substantially less basic than CMPO.

Figure 2:
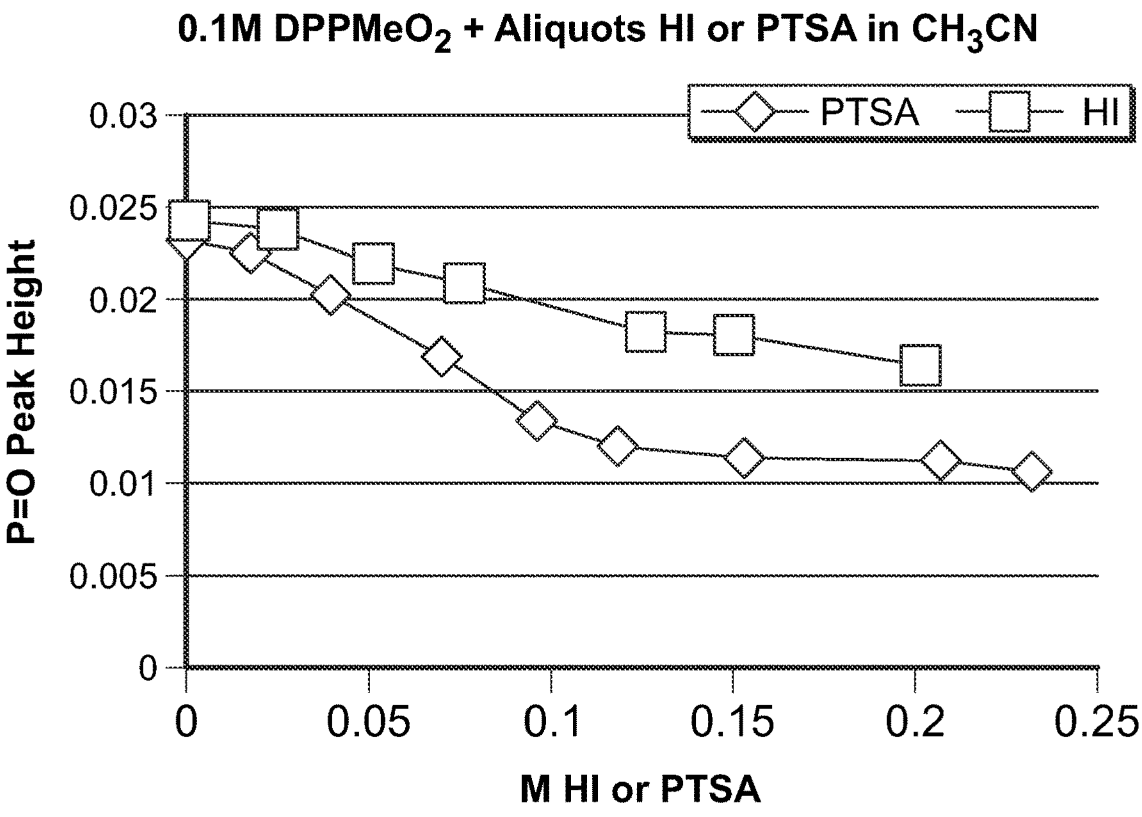
FIG. 2 is a graphical representation of bis(diphenylphosphino)methane dioxide (bis-$DPPMeO_2$) complexing with hydrogen iodide (HI) and p-toluenesulfonic acid (PTSA) in accordance with embodiments and/or techniques disclosed herein.
Figure 3:
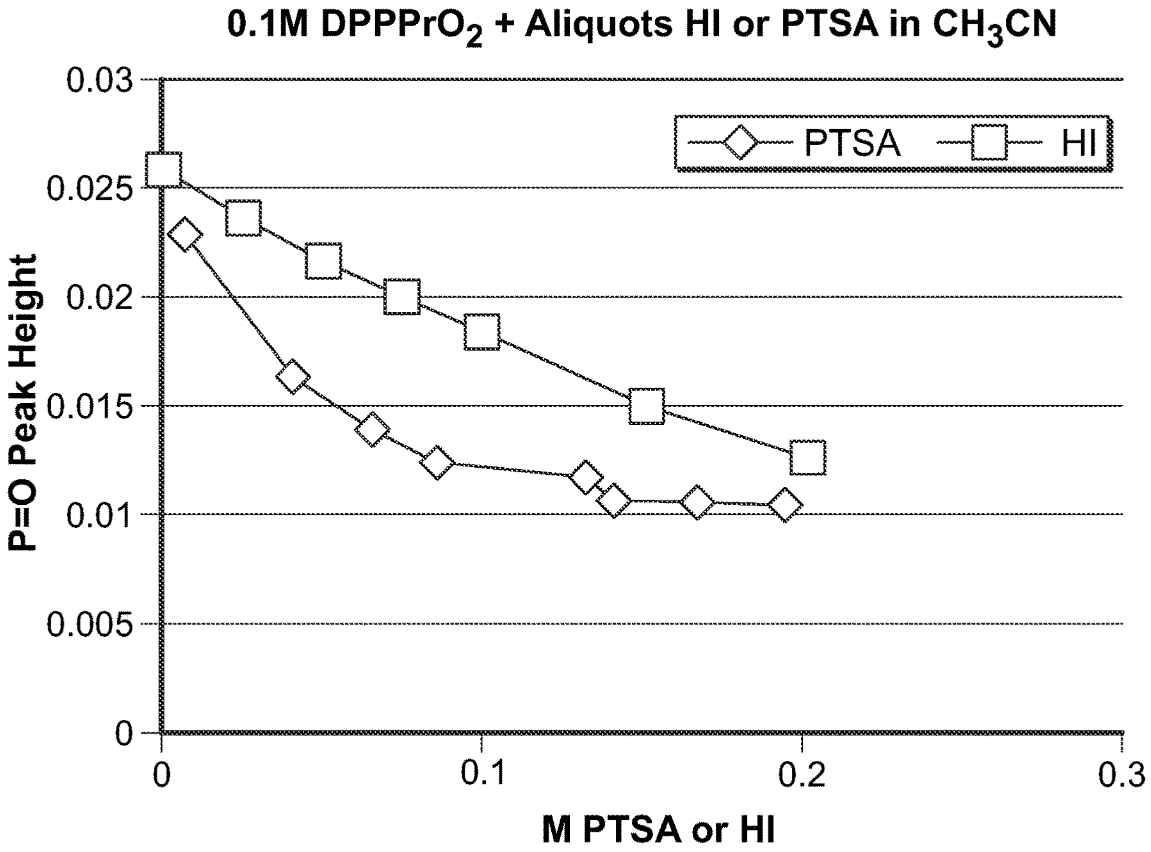
FIG. 3 is a graphical representation of bis(diphenylphosphino)propane dioxide (bis-$DPPPrO_2$) complexing with HI and PTSA in accordance with embodiments and/or techniques disclosed herein.

Room temperature investigations in acetonitrile showed surprisingly that while p-toluenesulfonic acid (PTSA) formed 1:1 complexes with the aforementioned three dioxides, in which the dioxides are complexing in bidentate fashion with the PTSA proton, HI formed 2:1 complexes in which the dioxides are complexing in a monodentate fashion. This is shown graphically in FIG. 2 for bis-DPPMe$O_2$ and FIG. 3 for bis-DPPPr$O_2$.

Figure 4:
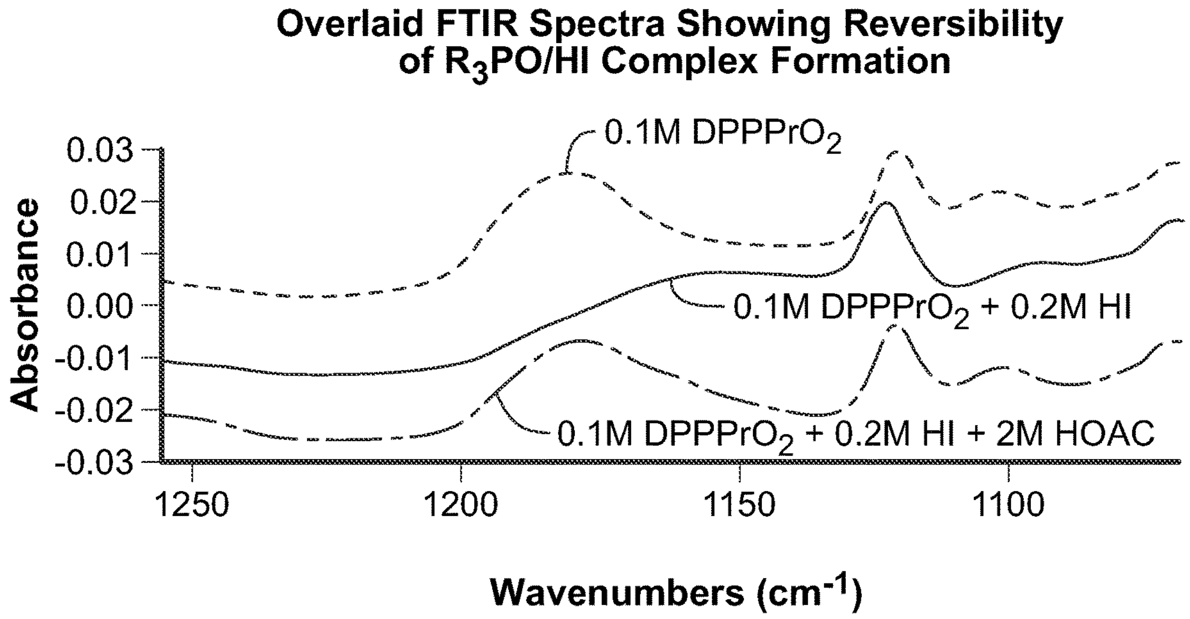
FIG. 4 is an overlaid graph of FTIR spectra of unreacted bis-$DPPPrO_2$, the HI-$DPPPrO_2$ adduct, and decomposition of the HI-$DPPPrO_2$ adduct after reaction with potassium acetate (KOAc) in accordance with embodiments and/or techniques disclosed herein.

To ensure that the phosphoryl group is fully intact after interaction with HI and that this interaction is reversible, the HI adducts were treated with a molar equivalence of potassium acetate (KOAc). Reversibility is indicated by free P═O groups reappearing as potassium iodide (KI) is formed. This was observed in all cases. In FIG. 4, the top spectrum is unreacted bis-DPPPr$O_2$, the middle spectrum is the HI-DPPPr$O_2$ adduct, and the bottom spectrum is after reacting the HI-DPPPr$O_2$ adduct with KOAc.

Vapor-Liquid-Equilibrium (VLE) Investigation

Figure 5:
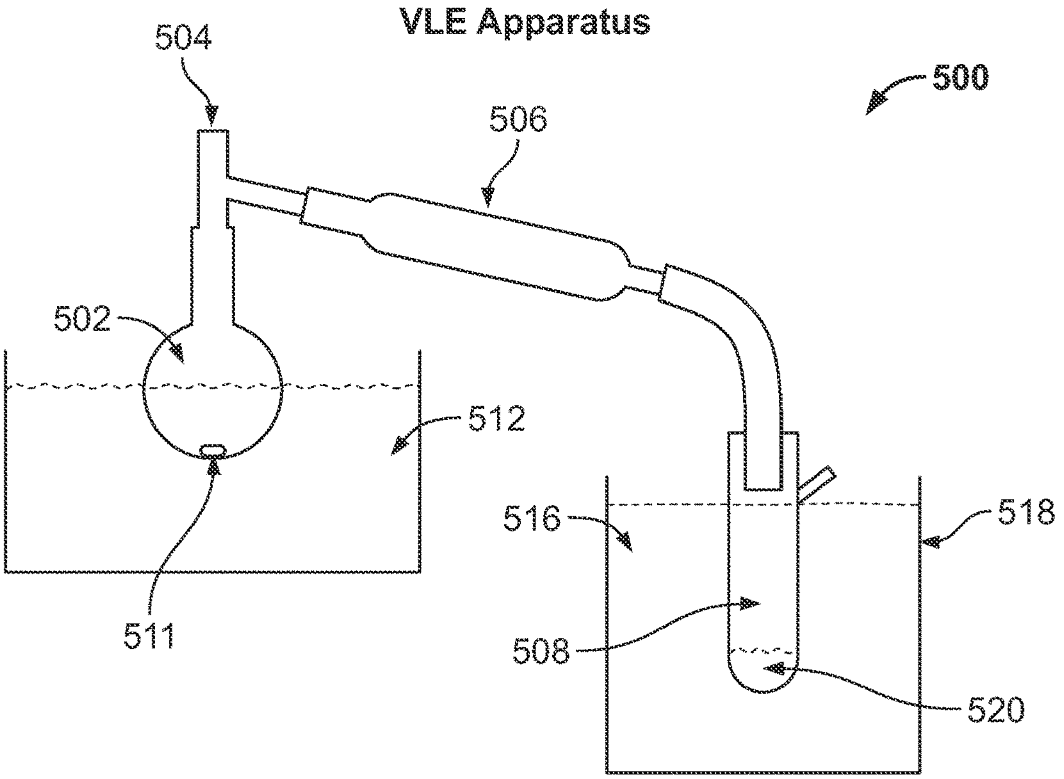
FIG. 5 is a drawing of a vapor-liquid-equilibrium (VLE) apparatus used for vapor-liquid-equilibrium testing in accordance with embodiments and/or techniques disclosed herein.

VLE experiments were carried out in a VLE apparatus 500 as illustrated in FIG. 5. The VLE apparatus 500 consists of a single neck 50 mL flat bottom flask (still pot) 502 to which a septum sealed distillation head 504, air condenser 506, receiving tube 508, and vent 509 are sequentially connected. The flat bottom flask 502 is immersed in an oil bath 512 maintained at 140° C. and those portions of the pot above the oil level, in addition to the distillation head 504 are wrapped with several layers of aluminum foil to ensure that condensation only occurs in the air condenser 506. All operations are carried out in air at atmospheric pressure.

The condensed vapor in the air condenser 506 is captured in a receiving tube 508 (10 mL Schlenk tube having graduations are every 0.2 mL) chilled in an ice bath 516. As the ice bath container consists of a clear beaker 518, visual determination of volume of condensate 520 collected can be made.

In all experiments, 25 mLs of starting solution of appropriate composition were prepared in a 25 mL volumetric flask. 20 mLs of this starting solution was then added via 20 ml disposable syringe to the VLE flask 502. The flask was connected to the remaining apparatus via ground glass joints and clamps, and then the VLE flask 502 was immersed in the pre-heated oil bath 512 and contents stirred with a magnetic stirrer 511. Appropriate parts of the VLE apparatus 500 were quickly wrapped in aluminum foil, after which evaporation of the liquid in the flat bottom flask 502 began in 5 to 10 minutes along with corresponding condensation in air condenser 506. When 2 mLs has been collected in the receiving tube 508, the distillation is terminated by removing the flat bottom flask 502 from oil bath 512. Collection of exactly 2 mLs of condensate in every experiment ensured that no bias is introduced into results as a function of variation in condensate volume. Receiving tube 508 contents are then syringed to a lidded sample tube for later iodide analysis.

As those skilled in the art of VLE data obtention will appreciate, it is critical that the VLE apparatus 500 operate in adiabatic fashion, in which only one equilibrium stage is present, and in which there is no enrichment of the vapor in the more volatile component by partial condensation. As such, the suitability of the VLE apparatus 500 in FIG. 5 was validated before use by determining the water concentration in the vapor condensate at flask water concentrations of 5 wt % and 10 wt % in acetic acid. The extent of enrichment of the more volatile water in the vapor phase upon heating the samples to reflux and upon analyzing a condensed vapor sample match well with previous literature values as shown in Table 2 where all values are expressed in mole fractions.

TABLE 2

| Validation of VLE Apparatus by Comparison with Prior Data | | | |
|---|---|---|---|
| Starting $H_2O$, Liq | $H_2O$, Vap | $H_2O$[1], Vap | $H_2O$[2], Vap |
| 0.15 | 0.25 | 0.23 | 0.23 |
| 0.28 | 0.42 | 0.41 | 0.40 |

[1]Results by process disclosed in European Pat. App. EP 0 506 240

[2]Results by process disclosed in Brown and A H Ewald, *Liquid-Vapour Equilibria. I. The Systems Carbon Tetrachloride-cyclo-hexane and Water-Acetic Acid*, Australian Journal of Scientific Research 3(2) 306-323

Iodide Analysis

Figure 6:
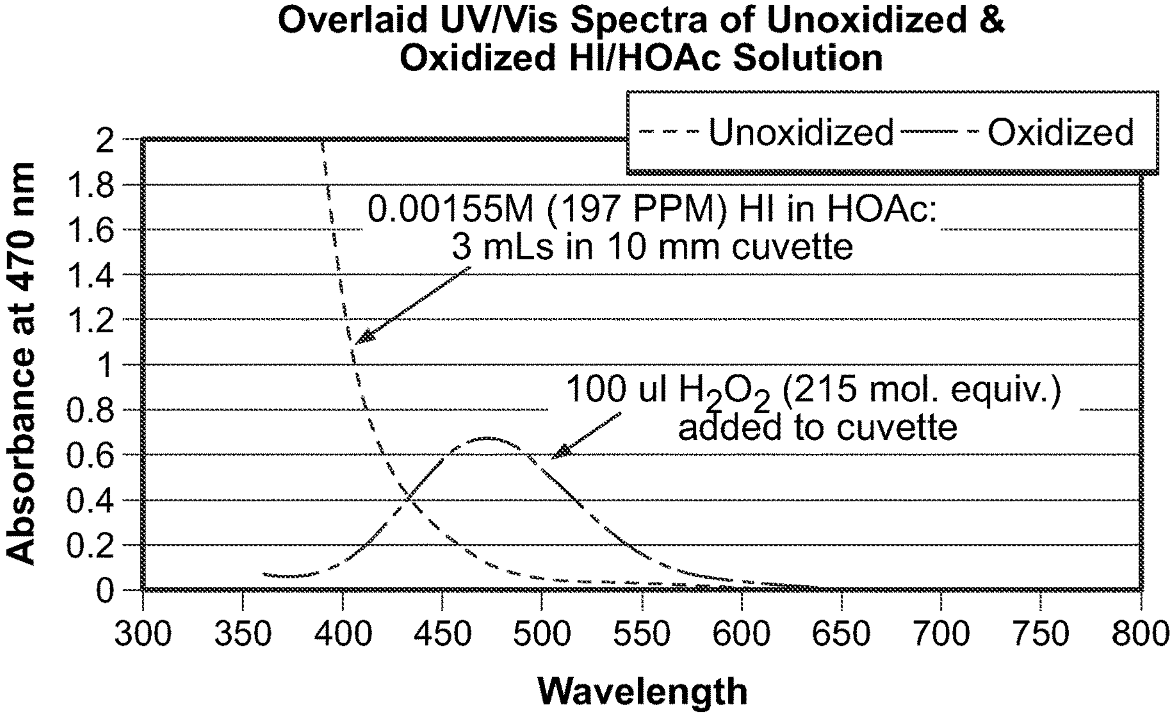
FIG. 6 is overlaid graph of UV/Vis spectra of unoxidized and oxidized hydrogen iodide/acetic acid solution in accordance with embodiments and/or techniques disclosed herein.

Quantification of iodide concentration in condensed vapor samples was carried out spectrophotometrically. Iodide in the sample was oxidized to molecular iodine by addition of hydrogen peroxide. Unlike iodide, which has no spectrophotometric features in GAA/$H_2O$ solutions, molecular iodine has a strong, fully resolved absorption band centered around 475 nm as shown in FIG. 6. Quantification accuracy of about ±20 ppm is possible.

FTIR Analysis

FTIR analyses were carried out on a Nicolet 6700 FTIR spectrometer equipped with a 3 bounce zinc selenide (ZnSe) attenuated total reflectance (ATR) crystal assembly. 0.1 mL aliquots of solution were removed from samples via micro-syringe. The solution was then placed on the crystal and an FTIR spectrum was obtained.

Examples 1-8

VLE experiments were carried out at 2 wt % $H_2O$ in the pot in order to simulate a low water process. As HI is a 57% aqueous solution and as in situ generation of the dioxides requires aqueous $H_2O_2$, in order to limit $H_2O$ to 2 wt % in the pot, all VLE runs were carried out at 0.1M HI. Table 3, below, contains the iodide concentrations measured in the condensed vapor phase for all VLE experiments, wherein test conditions 0.1M HI, 1.3M $H_2O$ (2 wt %), and GAA were used and were performed at approximately 140° C.

TABLE 3

| Example | Additive | Additive (molar conc.) | HI (ppm in vapor) |
|---|---|---|---|
| 1 | CMPO | 0.1 | 5,284 |
| 2 | CMPO | 0.2 | 855 |
| 3 | Bis-DPPMe$O_2$ | 0.05 | 7,889 |
| 4 | Bis-DPPPr$O_2$ | 0.05 | 6,291 |
| 5 | Bis-DPPPe$O_2$ | 0.05 | 5,392 |
| 6 | Bis-DPPMe$O_2$ | 0.1 | 876 |

TABLE 3-continued

| Example | Additive | Additive (molar conc.) | HI (ppm in vapor) |
|---|---|---|---|
| 7 | Bis-DPPPr$O_2$ | 0.1 | 421 |
| 8 | Bis-DPPPe$O_2$ | 0.1 | 683 |

Unlike the experiments at room temperature where HI formed 2:1 complexes in a monodentate fashion, these data show that at 140° C. the bidentate phosphine dioxides operate in a bidentate fashion with regard to interaction between P—O groups and HI. Examples 3-5, using the bidentate phosphine dioxides at 0.05M concentration, achieve similar suppression of HI volatilization as compared to Example 1, where the CMPO was used at a 0.1M concentration. Examples 6-8, using the bidentate phosphine dioxides at 0.1M concentration, achieve similar or increased suppression of HI volatilization as compared to Example 2, where the CMPO was used at a 0.2M concentration.

There is also strong evidence for increased stabilization arising from a chelating effect. The three phosphine dioxides of Examples 3-8, containing two phenyl groups and one alkyl group bonded to each P atom are electronically closer to TPPO than the CMPO, as indicated by the P═O frequencies shown in Table 1, above.

Figure 7:
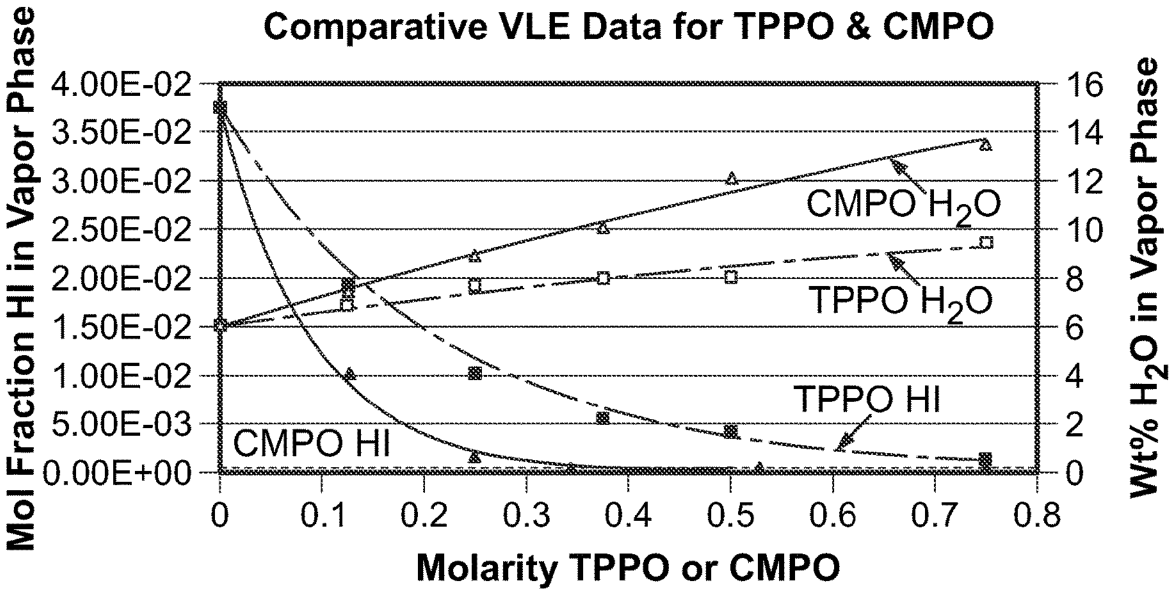
FIG. 7 is an overlaid graph of comparative VLE data for TPPO and CMPO (as defined in the examples) in accordance with embodiments and/or techniques disclosed herein.

FIG. 7 shows that at equivalent $R^3PO$ and HI molarities at 3.3 wt % $H_2O$, the CMPO has about a 5-fold increased ability to suppress HI volatilization. Test conditions for these VLE experiments were 0.25M HI, 3.3 wt % water, GAA, and variable amounts of $R^3PO$. Thus, the fact that the VLE data in the Table 3, above, show that at equivalent P—O group molarity, the three bidentate phosphine dioxides match the CMPO in terms of suppression of HI volatilization, is indicative of a chelate related stabilization effect.

In sum, the above experimental data indicate that bidentate phosphine dioxides as additives represent an improvement over the CMPO due to ability to operate at half CMPO concentration but with an equivalent suppression of HI volatility. When a molecular weight of about 420 g/mol for these bidentate phosphine dioxides as compared to 348 g/mol for the CMPO is taken into account, about 40% less by mass of these bidentate phosphine dioxides are required, thus freeing up increased reactor volume for production of acetic acid. Alternately, operation at an equivalent molarity to the CMPO will only lead to a slight decrease in available reactor volume while leading to a large decrease in volatilized HI. Both of these effects lead to improved ability to operate at reactor $H_2O$ concentration as low as 2 wt %.

Tertiary Arsine Oxide

Pentavalent Group 15 oxides having a larger central atom than phosphorus were analyzed based on the theory that increased polarizability and decreased electronegativity should lead to decreasing double bond character, increased ionicity, and increased basicity of the M═O group.

Triphenyl arsine oxide ($Ph_3AsO$) and triphenyl antimony oxide ($Ph_3SbO$) are both commercially available. In addition, another arsine oxide, cacodylic acid, shown below, is also commercially available and was analyzed to determine if the As═O group could function as a base while part of an acidic compound.

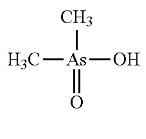

A further method of basicity manipulation involves replacement of the O atom, such as triphenylphosphine selenide ($Ph_3PSe$), which is commercially available.

$Ph_3SbO$ and $Ph_3PSe$ were eliminated as possible additives due to insolubility in GAA. Adding HI to slurries of these compounds in GAA did not lead to any solubility. Cacodylic acid was not soluble in GAA but upon addition of HI, complete solubilization occurred. $Ph_3AsO$ was soluble in GAA both with and without added HI.

Quantitative formation of the dioxide in GAA is assumed by virtue of heat liberated upon addition of the peroxide similar to in acetonitrile. Determination of P═O FTIR frequencies in acetonitrile as shown in the following Table 4, below, allows a gauge of basicity as lower frequency is associated with higher basicity.

TABLE 4

| $R_3PO$ | $pK_b$ | P═O, $cm^{-1}$ |
|---|---|---|
| TPPO | 3.16 | 1,191.6 |
| CMPO | 3.63 | 1,144.8 |
| $Ph_3AsO$ | 4.15 | 885.5 |

Figure 8:
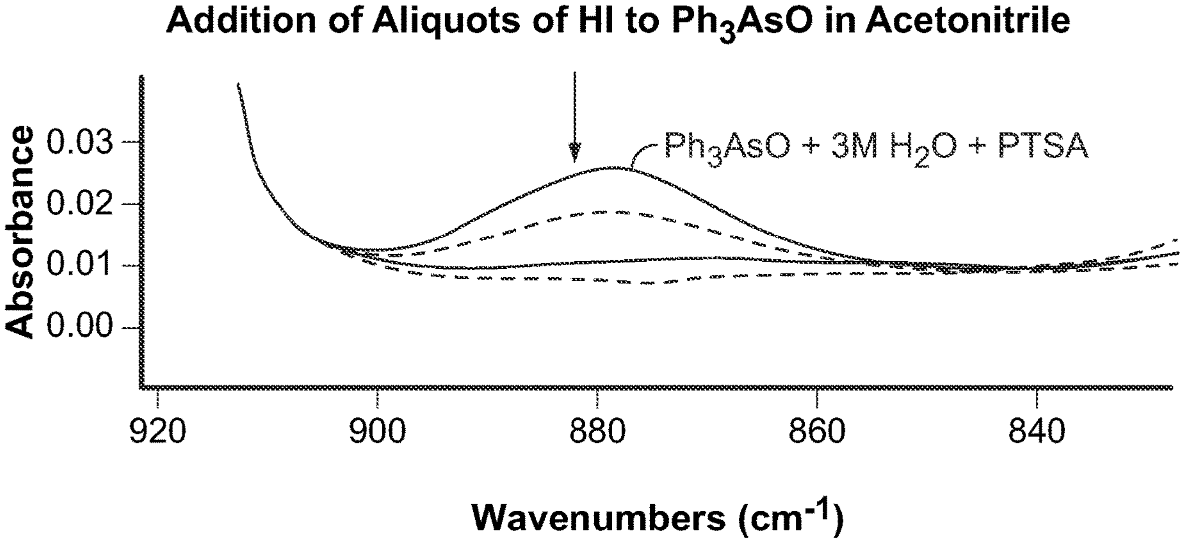
FIG. 8 is an overlaid graph of FTIR spectra showing complexing of triphenyl arsine oxide ($Ph_3AsO$) with HI in accordance with embodiments and/or techniques disclosed herein.
Figure 9:
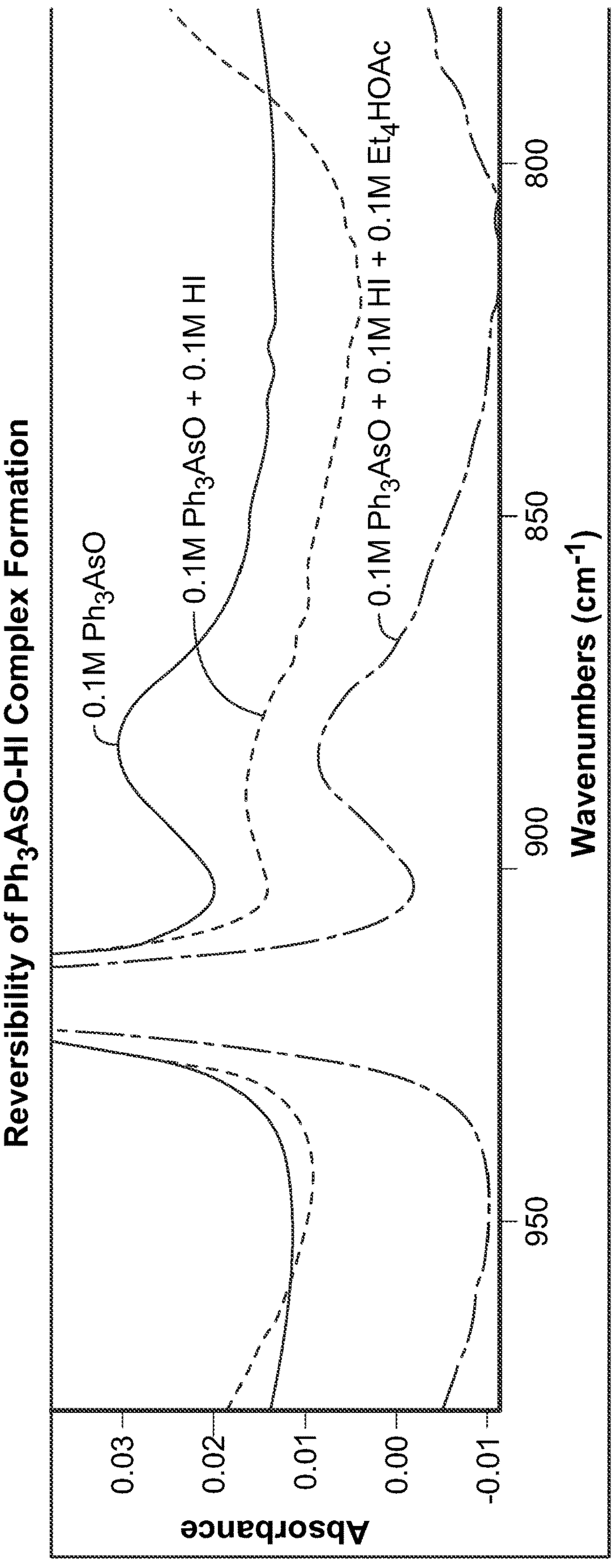
FIG. 9 is an overlaid graph of showing decomposition of the $Ph_3AsO$-HI adduct with the addition of tetraethyl ammonium acetate ($Et_4NOAc$) in accordance with embodiments and/or techniques disclosed herein.

The FTIR data in Table 4, above, obtained in acetonitrile solution show a much weakened P—O for $Ph_3AsO$ as compared to phosphine oxides, consistent with its expected increased basicity. The FTIR frequency of As═O at 885 $cm^{-1}$ is almost 300 wavenumbers lower than the CMPO. This is consistent with its $pk_b$ and indicates a base at least an order of magnitude stronger than the phosphine oxides. The 885 $cm^{-1}$ frequency was confirmed as the As═O stretch by its disappearance when aliquots of HI or PTSA were added and by its reappearance when KOAc or tetraethyl ammonium acetate ($Et_4NOAc$) were added to the HI or PTSA adducts. Some of these behaviors are shown in the overlaid FTIR spectra contained in FIG. 8 and FIG. 9. FIG. 8 shows the disappearance of the As═O frequency when aliquots of PTSA are added. A 1:1 interaction is observed regardless of $H_2O$ concentration. FIG. 9 shows the reappearance of the As═O frequency when aliquots of $Et_4NOAc$ were are added to the adduct.

Examples 9-13

A series of VLE runs were carried out under the conditions as shown in Table 5, below, in which 1:1 and 2:1 molar ratios of additive to HI were investigated. Of particular note was that at equivalent molarity, $Ph_3AsO$ is about 7 times more effective than the CMPO in suppressing volatilization of HI. In contrast, cacodylic acid showed only poor ability to suppress HI volatilization.

These data indicate that use of $Ph_3AsO$ as an additive represents an improvement over the CMPO as its enhanced suppression of HI volatility will allow lower $H_2O$ operation than that achievable with the CMPO.

TABLE 5

| Example | Additive | Additive (molar conc.) | HI (ppm in vapor) |
|---|---|---|---|
| 9 | CMPO | 0.25 | 7,693 |
| 10 | CMPO | 0.50 | 243 |
| 11 | $Ph_3AsO$ | 0.25 | 1,132 |
| 12 | Cacodylic acid | 0.25 | 22,721 |
| 13 | Cacodylic acid | 0.50 | 17,437 |

The scope of the present application is not intended to be limited to the particular embodiments of the processes, means, methods, and/or steps described in the specification. The particular embodiments disclosed above are illustrative only, as the process and system may be modified and practiced in different but equivalent manners apparent to those skilled in the art having the benefit of the teachings herein. Although the present invention and its advantages have been described in detail, it should be understood that various changes, substitutions and alterations can be made herein without departing from the spirit and scope of the invention as defined by the appended claims.

For the sake of brevity, only certain ranges are explicitly disclosed herein. However, in addition to recited ranges, any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, within a range includes every point or individual value between its end points even though not explicitly recited. Thus, every point or individual value may serve as its own lower or upper limit combined with any other point or individual value or any other lower or upper limit, to recite a range not explicitly recited.

All patents, test procedures, and other documents cited in this application are fully incorporated herein by reference for all jurisdictions in which such incorporation is permitted. In the event of conflict between one or more of the incorporated patents or publications and the present disclosure, the present specification, including definitions, controls.

What is claimed is:

1. A process for producing acetic acid in an acetic acid production system, comprising:

a) contacting methanol and carbon monoxide in the presence of a liquid reaction medium comprising iodide under carbonylation conditions sufficient to form acetic acid, wherein the liquid reaction medium comprises:
   i) a carbonylation catalyst, selected from the group consisting of rhodium catalysts, iridium catalysts and palladium catalysts;
   ii) water, in the range of from 0.1 wt % to 10 wt %, based on the weight of the liquid reaction medium; and
   iii) an additive at an additive to iodide molar ratio of 0.005:1 to 2.0:1, in-situ generated derivatives of the additive, or combinations thereof, wherein the additive comprises a bidentate phosphine dioxide, a tertiary arsine oxide, or a combination thereof; and
b) recovering the acetic acid.

2. The process of claim 1, wherein the additive is continually added as an acetic acid solution.

3. The process of claim 1, wherein the bidentate phosphine dioxide can be represented by Formula I:

Formula I

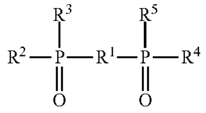

wherein:

P is phosphorous;

O is oxygen;

$R^1$ is selected from $C_1$-$C_{10}$ alkyls;

$R^2$, $R^3$, $R^4$, and $R^5$ are each independently selected from $C_4$-$C_{18}$ alkyls, $C_4$-$C_{18}$ aryls, $C_4$-$C_{18}$ cyclic alkyls, $C_4$-$C_{18}$ cyclic aryls, and combinations thereof, and can be the same as or different from one another; and each bidentate phosphine dioxide has at least 17 carbon atoms.

4. The process of claim 1, wherein the bidentate phosphine dioxide is selected from bis(diphenylphosphino)methane dioxide (bis-DPPMe$O_2$), bis(diphenylphosphino)propane dioxide (bis-DPPPr$O_2$), bis(diphenylphosphino) pentane dioxide (bis-DPPPe$O_2$), and combinations thereof.

5. The process of claim 1, wherein the bidentate phosphine dioxide has a phosphoryl group frequency of less than or equal to 1190 $cm^{-1}$ in acetonitrile at 25° C. as measured by Fourier transform infrared spectroscopy.

6. The process of claim 1, wherein the tertiary arsine oxide can be represented by Formula II:

Formula II

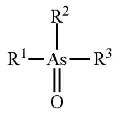

wherein:

As is arsenic;

O is oxygen; and $R^1$, $R^2$, and $R^3$ are each independently selected from $C_1$-$C_{10}$ alkyls, $C_4$-$C_{18}$ aryls, $C_4$-$C_{18}$ cyclic alkyls, $C_4$-$C_{18}$ cyclic aryls, and combinations thereof, and can be the same as or different from one another.

7. The process of claim 1, wherein the tertiary arsine oxide is selected from triphenyl arsine oxide (TPAsO), triethylarsine oxide (TEtAsO), and combinations thereof.

8. The process of claim 1, wherein the tertiary arsine oxide has a $pK_{BHX}$ less than or equal to 5.00, a $\Delta G°$ less than or equal to −20 KJ $mol^{-1}$, or a combination thereof, wherein $pK_{BHX}$ and $\Delta G°$ are measure in $CCl_4$ at 25° C.

9. The process of claim 1, wherein the additive exhibits a melting point of less than 100° C.

10. The process of claim 1, wherein a molar ratio of the additive to the carbonylation catalyst is greater than about 0.5:1.

11. A method for reducing water in an acetic acid production process, comprising:

a) contacting methanol and carbon monoxide in the presence of a liquid reaction medium comprising a first amount of hydrogen iodide, under carbonylation conditions sufficient to form acetic acid, wherein the liquid reaction medium comprises:

i) a carbonylation catalyst, selected from the group consisting of rhodium catalysts, iridium catalysts and palladium catalysts; and ii) a first amount of water, sufficient to form an azeotropic mixture of the first amount of hydrogen iodide and the first amount of water; and b) adding an additive to the liquid reaction medium at an additive to iodide molar ratio of 0.005:1 to 2.0:1, wherein:

i) the additive forms a complex with at least a portion of the first amount of hydrogen iodide resulting in a second amount of hydrogen iodide; and ii) the additive comprises a bidentate phosphine dioxide, a tertiary arsine oxide, or a combination thereof;

c) reducing the water in the liquid reaction medium to a second amount of water while maintaining an azeotropic mixture of the second amount of hydrogen iodide and the second amount of water.

12. The method of claim 11, wherein the additive is continually added as an acetic acid solution.

13. The method of claim 11, wherein the bidentate phosphine dioxide can be represented by Formula I:

Formula I

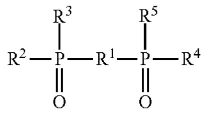

wherein:

P is phosphorous;

O is oxygen;

$R^1$ is selected from $C_1$-$C_{10}$ alkyls;

$R^2$, $R^3$, $R^4$, and $R^5$ are each independently selected from $C_4$-$C_{18}$ alkyls, $C_4$-$C_{18}$ aryls, $C_4$-$C_{18}$ cyclic alkyls, $C_4$-$C_{18}$ cyclic aryls, and combinations thereof, and can be the same as or different from one another; and each bidentate phosphine dioxide has at least 17 carbon atoms.

14. The method of claim 11, wherein the bidentate phosphine dioxide is selected from bis(diphenylphosphino)methane dioxide (bis-DPPMe$O_2$), bis(diphenylphosphino)propane dioxide (bis-DPPPr$O_2$), bis(diphenylphosphino) pentane dioxide (bis-DPPPe$O_2$), and combinations thereof.

15. The method of claim 11, wherein the bidentate phosphine dioxide has a phosphoryl group frequency of less than or equal to 1190 $cm^{-1}$ in acetonitrile at 25° C. as measured by Fourier transform infrared spectroscopy.

16. The method of claim 11, wherein the tertiary arsine oxide can be represented by Formula II:

Formula II

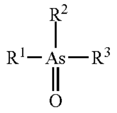

wherein:

As is arsenic;

O is oxygen; and $R^1$, $R^2$, and $R^3$ are each independently selected from $C_1$-$C_{10}$ alkyls, $C_4$-$C_{18}$ aryls, $C_4$-$C_{18}$ cyclic alkyls, $C_4$-$C_{18}$ cyclic aryls, and combinations thereof, and can be the same as or different from one another.

17. The method of claim 11, wherein the tertiary arsine oxide is selected from triphenyl arsine oxide (TPAsO), triethylarsine oxide (TEtAsO), and combinations thereof.

18. The method of claim 11, wherein the tertiary arsine oxide has a $pK_{BHX}$ less than or equal to 5.00, a $\Delta G°$ less than or equal to −20 kJ $mol^{-1}$, or a combination thereof, wherein $pK_{BHX}$ and $\Delta G°$ are measure in $CCl_4$ at 25° C.

19. The method of claim 11, wherein the additive exhibits a melting point of less than 100° C.

20. The method of claim 11, wherein a molar ratio of the additive to the carbonylation catalyst is greater than about 0.5:1.

* * * * *